United States Patent [19]

Ting et al.

[11] Patent Number: 5,182,289
[45] Date of Patent: Jan. 26, 1993

[54] HETEROBICYCLIC COMPOUNDS HAVING ANTIINFLAMMATORY ACTIVITY

[75] Inventors: Pauline C. Ting, Morristown; Margaret H. Sherlock, Bloomfield; Wing C. Tom, Cedar Grove; James J. Kaminski, Long Valley, all of N.J.

[73] Assignee: Schering Corporation, Kenilworth, N.J.

[21] Appl. No.: 623,710

[22] PCT Filed: Jun. 12, 1989

[86] PCT No.: PCT/US89/02502
§ 371 Date: Dec. 10, 1990
§ 102(e) Date: Dec. 10, 1990

Related U.S. Application Data

[63] Continuation-in-part of Ser. No. 206,550, Jun. 14, 1988.

[51] Int. Cl.$^5$ .................. A61K 31/435; C07D 471/04
[52] U.S. Cl. .................................... 514/278; 514/300; 546/15; 546/113; 544/236; 544/280; 544/350; 548/153; 548/207; 548/453; 548/303.1; 548/360.5; 548/301.1; 548/357.5
[58] Field of Search ................. 546/113, 15; 514/300, 514/278

[56] References Cited

FOREIGN PATENT DOCUMENTS 0164860 12/1985 European Pat. Off. .
0257102 3/1988 European Pat. Off. .
1196205 7/1985 Fed. Rep. of Germany .
51-68571 6/1976 Japan .

OTHER PUBLICATIONS

Ficken et al., J. Chem. Soc., pp. 747–748 (1961).
Adler et al., J. Med. Chem. 6(5) pp. 480–483 (1963).
Tetrahedron Letters vol. 28, No. 35, pp. 4027–4030 (1987).
Journal of the American Chemical Society vol. 81, No. 1, pp. 740–743 (1959).
Arzneimittel Wirkungen pp. 46, 54, 55 (1981).
Advanced Organic Chemistry Second Edition McGraw Hill pp. 146–150 (1977).

Primary Examiner—Bernard Dentz
Attorney, Agent, or Firm—James R. Nelson; Edward H. Mazer; Paul A. Thompson

[57] ABSTRACT

Heterobicyclic and heterocyclic intermediate compounds and their use in treating inflammation, hyperproliferative skin conditions such as psoriasis and allergy are disclosed.

20 Claims, No Drawings

HETEROBICYCLIC COMPOUNDS HAVING ANTIINFLAMMATORY ACTIVITY

CROSS REFERENCE TO RELATED APPLICATIONS

This application is a continuation-in-part of U.S. Ser. No. 206,550 filed Jun. 14, 1988 which was filed as international patent application no. PCT/US89/02502.

BACKGROUND OF THE INVENTION

The present invention relates to certain heterobicyclic compounds having antiinflammatory activity and antiallergic conditions and to pharmaceutical compositions and methods employing such compounds.

U.S. Pat. No. 4,569,942 discloses certain 2-oxindole-1-carboxamide compounds having an acyl substituent at the 3-position as having analgesic and antiinflammatory activities.

European published patent Application No. 0 175 551 discloses 1,3-diacyl-2-oxindole compounds, while European published patent Application Nos. 0 181 136 and 0 173 520 disclose substituted 2-oxindole-3-carboxamides and tricyclic and quadracyclic compounds including the 2-oxindole-3-carboxamide unit as antiinflammatory agents.

The art also includes numerous disclosures of 3,3-disubstituted 2-oxindoles, as pharmaceutically active compounds, e.g. British Patent No. 1,132,318, Dutch Patent Application No. 6604752 (anti-inflammatory), and South African Patent 68-01099 (antidepressants).

1,3-dihydro-3,3-dimethyl-2H-[2,3-b]-pyridin-2-one is disclosed by Ficken et al. in *J. Chem. Soc.*, 747-89 (1961). No pharmaceutical utility is mentioned for the compound.

Pyrrolidinopyridine derivatives having geminal substitution are disclosed in *Chem. Abstracts*, Vol. 77, No. 19, Abst. No. 12637e (1972). No pharmaceutical activity is disclosed.

Japanese Patent Application 51068571 discloses compounds of the formula

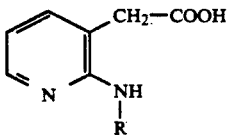

wherein R is substituted phenyl, and are useful for inflammatory conditions.

SUMMARY OF THE INVENTION

It has now surprisingly been found that compounds of formulas (I) and (II) below have particularly advantageous properties useful in the treatment of inflammation or allergies by inhibiting the formation of lipoxygenase and cyclooxygenase derived products of arachidonic acid metabolism. The compounds of formulas (I) and (II) are represented by the structural formulas:

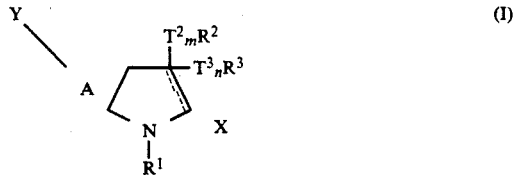

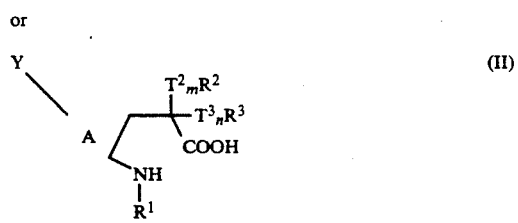

or a pharmaceutically acceptable salt or solvate thereof, wherein

A represents a fused 5- or 6-membered heterocyclic aromatic ring containing 1 to 3 heteroatoms in the ring, each heteroatom independently represents O, S, N or $NR^6$ wherein $R^6$ in the group $NR^6$ is hydrogen or $C_1$ to $C_4$ alkyl;

the dotted lines represent optional double bonds, such that when the bond to X is a double bond, X is O or S; and when the bond to X is a single bond, X is $-OR^{10}$ wherein $R^{10}$ is alkyl or aralkyl;

$T^2$ and $T^3$ independently represent S, SO or $SO_2$;

m and n independently represent 0 or 1;

$R^1$ represents hydrogen, alkyl, aryl, aralkyl, or a 5- or 6-membered heterocyclic aromatic ring having from 1 to 3 heteroatoms in the ring, each heteroatom independently selected from $NR^6$, O, S or N atoms;

$R^2$ and $R^3$ independently represent hydrogen with the proviso at least one of $R^2$ and $R^3$ is not hydrogen;

alkyl;
cycloalkyl;
halogen;
haloalkyl;
hydroxyalkyl;
alkoxyalkyl;
aryl;
aralkyl;
$COR^7$ wherein $R^7$ is alkyl, aryl or aralkyl;

and with the further proviso that when $T^2$ or $T^3$ is S, SO or $SO_2$ that $R^2$ or $R^3$ is not hydrogen or halogen;

$-D-OCO-R^4$ wherein D represents an alkylene group having from 1 to 4 carbon atoms and $R^4$ is alkyl, aryl or aralkyl;

a $C_3$ to $C_7$ spirocarbocyclic ring whereby $R^2$ and $R^3$ are joined together;

the rings represented by A, $R^1$, aryl or aralkyl may each be optionally substituted by up to three Y substituents;

wherein each Y substituent independently represents $-OH$, hydroxyalkyl, alkyl, halogen, $-NO_2$, alkoxy, alkoxyalkyl, alkylthio, $-CF_3$, $-CN$, cycloalkyl, alkynyloxy, alkenyloxy, $-S(O)_p-R^4$ (wherein $R^4$ is defined above and p is an integer from 0 to 2), $-CO-R^5$ (wherein $R^5$ represents $-OH$, $-NH_2$, $-NHR^4$, $N(R^4)_2$ or $-OR^4$ in which $R^4$ is as defined above), $-O-D-COR^5$ (wherein D is defined above and $R^5$ is as defined above), $-NH_2$, $-NHR^4$, $-N(R^4)_2$ (wherein $R^4$ is as defined above) or $-NHC(O)H$.

As used herein, the terms below have the following meaning, unless otherwise indicated:

halogen—represents fluoro, chloro, bromo or iodo;

alkyl (including the alkyl portions of alkoxy, alkylthio, alkylsulfinyl or alkylsulfonyl)—represents straight and branched hydrocarbon chains and contains from 1 to 6, preferably 1 to 4, carbon atoms; for example methyl (ie. —CH$_3$), ethyl, propyl, isopropyl, butyl, iso-butyl, tert-butyl, pentyl, hexyl and the like.

alkenyloxy—represents straight and branched hydrocarbon chains having at least one carbon to carbon double bond, and unless otherwise specified, contains from 3 to 6 carbon atoms, the alkenyl group thereof being bonded to an adjacent structural element through an oxygen atom;

alkynyloxy—represents straight and branched hydrocarbon chains having at least one carbon to carbon triple bond, and unless otherwise specified, contains from 3 to 6 carbon atoms, the alkynyl group thereof being bonded to an adjacent structural element through an oxygen atom;

alkylene—represents divalent, straight or branched hydrocarbon chains having from 1 to 4 carbon atoms, such alkylene group being bonded to two adjacent structural elements from the same or different carbon atoms;

substituted phenyl—represents a phenyl group substituted with one to three Y groups and the Y groups may be the same or different;

cycloalkyl—represents saturated carbocyclic rings having from 3 to 7 carbon atoms, for example cyclopropyl, cyclobutyl, cyclopentyl, cyclohexyl and the like;

alkoxy—represents an alkyl moiety containing from 1 to 6 carbon atoms covalently bonded to an adjacent structural element through an oxygen atom, such as for example, methoxy (ie. —OCH$_3$), ethoxy, propoxy, isopropoxy, butoxy, pentoxy, hexoxy and the like;

spirocarbocyclic ring—a cycloalkyl moiety containing 3 to 7 carbon atoms covalently bonded to an adjacent structural element through one carbon atom in the cycloalkyl moiety;

aryl—represents a carbocyclic moiety containing at least one benzenoid-type ring, with the aryl groups preferably containing from 6 to 15 carbon atoms, for example, phenyl, napthyl, indenyl, indanyl, and the like.

aralkyl—represents an aryl moiety of 6 to 15 carbon atoms covalently bonded to an alkyl moiety of one to six carbon atoms such as, for example, benzyl, phenylethyl, and the like;

trifluoromethyl—represented by —CF$_3$;

cyano—represented by —CN;

nitro—represented by —NO$_2$;

hydroxyalkyl—an alkyl moiety in which one or more of the hydrogens is replaced by a hydroxy moiety, such as, for example, hydroxymethyl (i.e. —CH$_2$OH), hydroxyethyl, 1-hydroxypropyl, 2-hydroxypropyl, 3-hydroxypropyl, 4-hydroxyhexyl and the like.

alkylthio—refers to an alkyl group bonded to a sulfur atom, for example, methylthio (ie. CH$_3$S—), ethylthio and the like.

alkylsulfinyl—refers to an alkyl group bonded to a sulfinyl group, for example methylsulfinyl(ie. CH$_3$SO—), ethylsulfinyl and the like alkylsulfonyl—refers to an alkyl group bonded to a sulfonyl group, for example, methylsulfonyl(ie.CH$_3$SO$_2$—), ethylsulfonyl and the like.

alkoxyalkyl—represents an alkoxy moiety of 1 to 6 carbon atoms covalently bonded to an adjacent structural element through an alkyl moiety of 1 to 6 carbon atoms.

heterocyclic aromatic ring (R$^1$)—represents cyclic groups having at least one NR$^6$, O, S and/or N in the ring structure and having a sufficient number of delocalized pi electrons to provide aromatic character, with the aromatic heterocyclic groups, preferably containing from 2 to 14 carbon atoms, e.g., 2-, 3- or 4- pyridyl, 2- or 3-furyl, 2- or 3-thienyl, 2-, 4-or 5-thiazolyl, 2-or 4-imidazoyl, 2-, 4- or 5-pyrimidinyl, 2-pyrazinyl, 3- or 4-pyridazinyl, 3-,5- or 6-[1,2,4-triazinyl], 2-, 3-, 4-, 5-, 6- or 7-benzofuranyl, 2-, 3-, 4-, 5-, 6- or -7-indolyl, 3-, 4- or 5-pyrazolyl, 2-, 4- or 5-oxazoyl, and the like, with all available suitable carbon atoms thereof being intended as a possible points of attachment to the N atom; and the fused 5- or 6-membered heterocyclic aromatic group (A)—represents cyclic groups having at least one O, S, N and/or NR$^6$ in the ring structure and having a sufficient number of delocalized pi electrons to provide aromatic character, preferably containing from 2 to 6 carbon atoms, e.g. a fused thiophene, furan, pyrrole, imidazole, pyrazole, pyridine, pyrazine, pyrimidine, pyridazine, isothiazole, isoxazole, oxazole, and the like, with all possible isomeric variations thereof being intended as being with the scope of this invention.

The preferred meaning of R$^1$ is C$_1$ to C$_4$ alkyl, phenyl, substituted phenyl, 2-, 3- or 4-pyridyl, 2- or 3-furyl, 2- or 3-thienyl, 2-, 4- or 5-thiazoyl and 2- or 4-imidazolyl with phenyl and substituted phenyl being most preferred.

The preferred meaning of A is

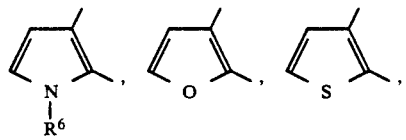

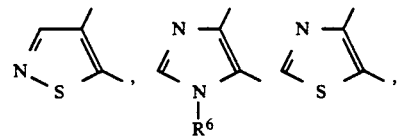

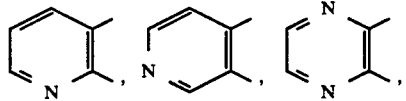

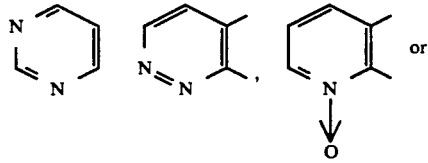

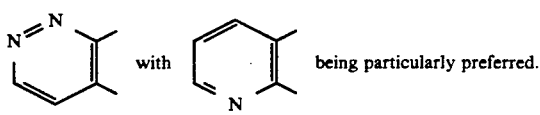

A most preferred group of compounds is characterized by the general formula (Ii)

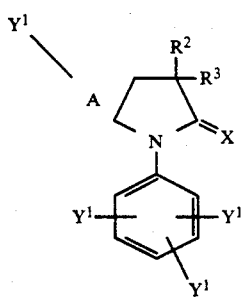

wherein A represents a pyridine ring, and each Y defined as $Y^1$ independently represents hydrogen, halogen preferably chloro or fluoro, alkoxy preferably methoxy, alkylthio preferably methylthio, alkylsulfinyl preferably methylsulfinyl, or alkylsulfonyl preferably methylsulfonyl; and $R^2$ and $R^3$ (ie. m and n are zero) independently represent methyl, ethyl or fluoro, and X is O or S, preferably O wherein the $Y^1$ substituent(s) can be in any available position(s).

The preferred meaning of A is

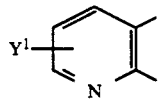

wherein $Y^1$ is as above defined. Compounds wherein $R^2$ and $R^3$ both represent methyl or ethyl or one represents methyl or ethyl and the other is halogen, preferably fluoro, are particularly useful.

Another preferred group of compounds is characterized by the formula:

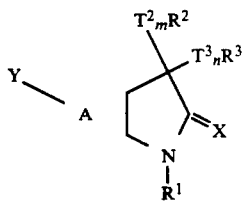

wherein Y, ring A, $T^2$, $T^3$, m, n, $R^1$, $R^2$ and $R^3$ are as defined hereinbefore. Preferably, the preferred meaning of ring A is

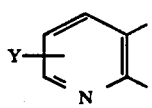

Also preferred is that X is O, more preferably where $T^2$ is S and n is zero.

Another preferred group of compounds is characterized by the general formula

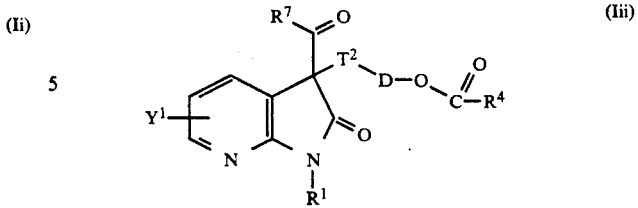

wherein $Y^1$, $R^7$, $T^2$, D, $R^1$ and $R^4$ are as defined hereinbefore. Most preferably $Y^1$ is hydrogen, $R^1$ is phenyl, D is —$(CH_2)_2$—, $T^2$ is S, and $R^4$ and $R^7$ are methyl, otherwise known as 1,3-dihydro-3-(2-acetoxy-ethylthio)-3-(1-oxoethyl)-N-phenyl-2-H-pyrrolo(2,3-b)pyridin-2-one.

Another preferred group of compounds is characterized by the general formula

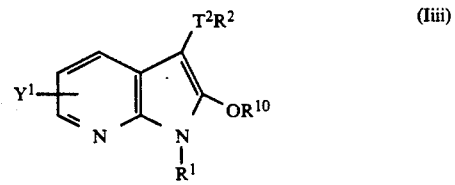

wherein $Y^1$, $R^1$, $R^{10}$, $T^2$ and $R^2$ are as defined hereinbefore. Most preferably, $Y^1$ is hydrogen, $R^1$ and $R^2$ are phenyl, $T^2$ is S and $R^{10}$ is methyl. Preferably $Y^1$ is hydrogen, A is 2-, 3-pyridyl and $R^1$ represents halophenyl, more preferably chlorophenyl, most preferably 4-chlorophenyl, m and n are zero and $R^2$ and $R^3$ are methyl.

Another preferred group of compounds is characterized by the general formula

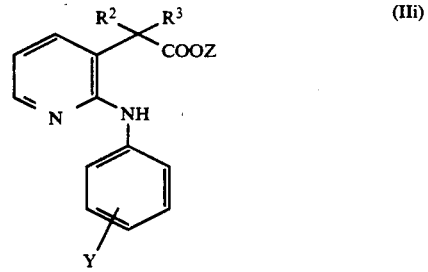

wherein $R^2$ and $R^3$ are as defined hereinbefore and Z is a hydrogen atom or a salt such as sodium, potassium and the like.

A number of the compounds may contain an asymmetric center and thus can exist in optically active stereoisomeric forms such as the R and S enantiomer forms. The various mixtures and racemates of the above isomers are within the scope of the present invention.

Certain compounds of the invention can also form pharmaceutically acceptable salts with organic and inorganic acids, e.g., a pyrido- or pyrazino-nitrogen atoms may form salts with strong acid, while compounds having basic Y substituents such as amino groups also form salts with weaker acids. Examples of suitable acids for salt formation are hydrochloric, sulfuric, phosphoric, acetic, citric, oxalic, malonic, salicyclic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from the respective salt forms somewhat in certain physical properties, such as solubility in polar solvents, but the salts are otherwise equivalent to their respective free base forms for purposes of the invention.

Also, some compounds of this invention are acidic, e.g., when Y is OH, and can form salts with inorganic and organic bases.

The compounds of formulas I and II may be prepared by general processes known in the art. Basically, the processes comprise either adding one or more of the substituents $R^1$, $R^2$ and $R^3$ to the existing fused ring nucleus or completing the fused ring structure by an intramolecular condensation. Such processes can be illustrated by the reaction schemes A to N below, in which $R^1$, $R^2$, $R^3$, X and A are as defined above, unless otherwise indicated.

A. Preparation of a compound of formula I wherein $R^2$ and $R^3$ are the same:

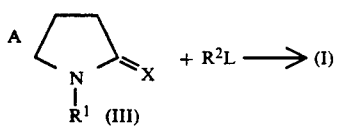

The process is preferably carried out by first adding the base (e.g. sodium hydride, potassium hydride, lithium diisopropylamide, lithium hexamethyldisilazide) to III in an inert solvent (e.g. ether such as diethyl ether, tetrahydrofuran, dioxane or polar aprotic solvents such as N,N-dimethylformamide, N,N-dimethylacetamide, dimethylsulfoxide), preferably under an inert atmosphere ($N_2$), followed by addition of $R^2L$ wherein L represents a good leaving group, e.g., when $R^2$ is lower alkyl, L can be chloride, bromide, iodide, mesylate, tosylate, etc. Any suitable temperature can be used. Preferably, the various steps of the reaction are carried out at temperatures between 0° C. and 25° C. When the process is used for introducing halogen, $R^2L$ represents halogenating agents such as $Br_2$, $Cl_2$, diethylaminosulfurtrifluoride (DAST) or N-bromosuccinimide.

B. For production of compounds wherein $R^2$ and $R^3$ are the same or different:

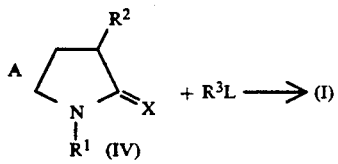

The process is carried out in the same manner with the same reagents and under the same conditions as under process A.

C. Compounds of formula (I) wherein X is O can be prepared by the following reaction:

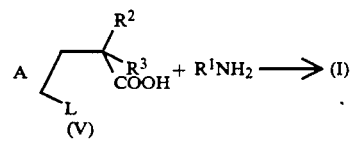

This ring closure reaction can be carried out by treating the acid (V) or a reactive derivative thereof with a suitable condensation reagent. For example, the reaction could be carried out by the use of paratoluenesulfonic acid. A further possibility is first to activate the acid by reaction with a halogenating agent and the amine with a base. The halogenating agents, bases and solvents referred to above (e.g., process A) may be used. The preferred solvents for the dehydration reaction are higher boiling protic solvents such as pentanol and hexanol.

D. In the preparation of compounds wherein X is O:

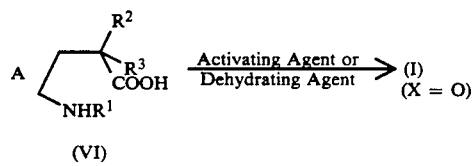

This intramolecular ring closure reaction may be performed by treating VI with an activating agent such as acetic acid, trifluoroacetic acid or propionic acid or a dehydrating agent such as dicyclohexylcarbodiimide or 1-ethyl-3-(3-dimethylaminopropyl)-carbodiimide in an inert solvent such as chlorinated hydrocarbons (e.g., dichloromethane, 1,2-dichloroethane, chloroform) or ethers (e.g., diethyl ether, tetrahydrofuran or dioxane) at temperatures ranging from 0° to 25° C.

E. For the preparation of compounds wherein X=S:

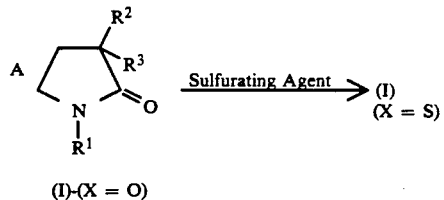

As is obvious to one skilled in the art this exchange of sulfur for oxygen can possibly be carried out at an earlier stage in the preparation of the final compounds, e.g. where preparing some of the starting compounds (III) to (VIII). The replacement of oxygen by sulfur can be achieved by treating the starting compound with any suitable sulfurylating agent, e.g. Lawesson's reagent or $P_2S_5$ in a suitable solvent, e.g. toluene, benzene or xylene at elevated (reflux) temperatures, e.g., 110° C. to 140° C.

F. Preparation of compounds wherein $R^1$ represents alkyl:

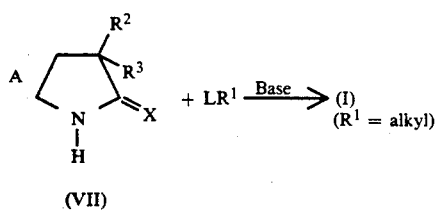

(VII)

The process is carried out by first treating (VII) with a base and thereafter adding the alkylating reagent LR¹. The bases, alkylating agents and solvents used may be the same as those referred to above, e.g. under process A.

G. Preparation of compounds wherein $R^1$, $R^2$ and $R^3$ are all the same alkyl group:

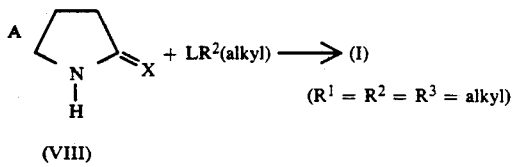

(VIII)

This alkylation reaction can be conveniently carried out by using standard procedures, e.g. similar to those described under process A.

H. Preparation of compounds wherein $T^2$ is S:

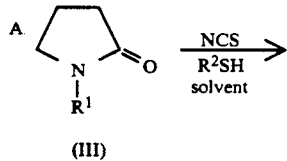

(III)

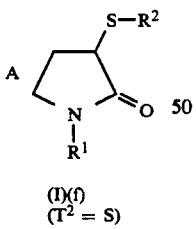

(I)(f)
($T^2$ = S)

Compound (I)(f) wherein $T^2$ is S can be prepared by treating a compound of formula (III) with N-chlorosuccinimide (NCS) and any suitable sulfide in any suitable solvent. Such solvents include the chlorinated hydrocarbons cited above, preferably chloroform, or ether solvents such as diethyl ether, tetrahydrofuran, dioxane and the like. The reaction can be carried out at temperatures ranging from 0° C. to about 25° C.

I. Preparation of compounds wherein $T^2 = T^3 = S$ and $R^2$ is different from $R^3$:

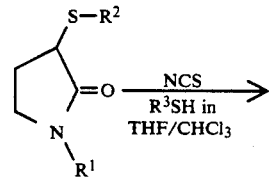

(f)

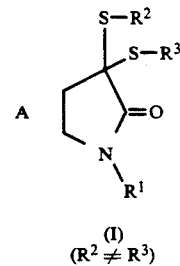

(I)
($R^2 \neq R^3$)

Compound (f) can be prepared using essentially the same reagents and process conditions as described in process H above.

J. Preparation of compounds wherein $T^2 = T^3 = S$ and $R^2 = R^3$:

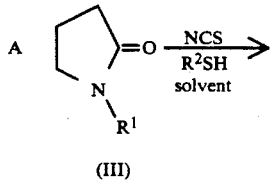

(III)

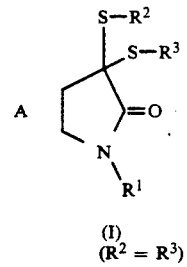

(I)
($R^2 = R^3$)

Compound (I) wherein $R^2 = R^3$ can be prepared by treating a compound of formula (III) with N-chlorosuccinimide (NCS) and any suitable sulfide in any suitable solvent. Such solvents include the chlorinated hydrocarbons cited above, or ether solvents such as diethyl ether, tetrahydrofuran, dioxane and the like. The reaction can be carried out at temperature ranging from 0° C. to about 25° C.

K. Preparation of compounds wherein $T^2$ is SO:

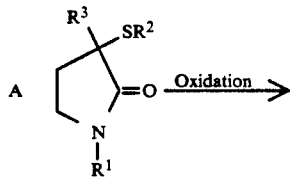

(I)
($T^2$ = S)

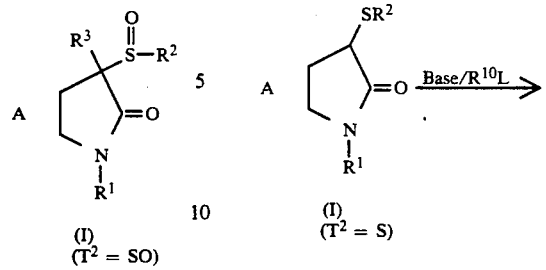

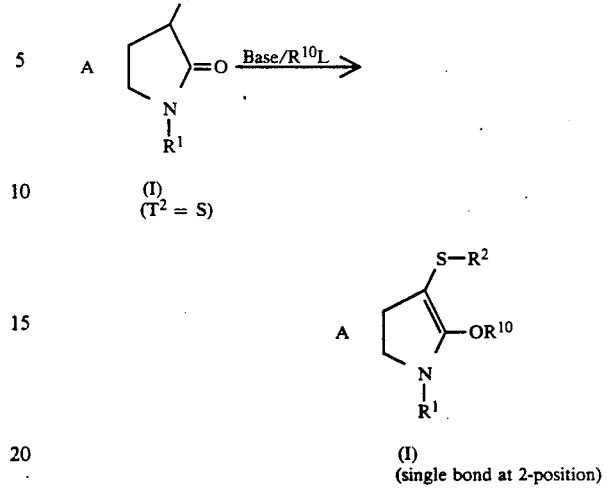

Compound (I) wherein $T^2=S$ is treated with any suitable oxidizing agent to oxidize S to SO such as, for example m-chloroperoxybenzoic acid, hydrogen peroxide, sodium periodate, sodium perborate, and the like. The solvent employed will vary, depending upon the oxidation agent. Representative solvents include the chlorinated hydrocarbons such as dichloromethane, 1,2-dichloroethane, chloroform and the like; and can include protic solvents such as water, methanol or ethanol. The reaction can be carried out at temperatures in the range of 0° C. to ambient, preferably about 25° C. to give compound (I) wherein $T^2$ is SO.

L. Preparation of compounds wherein $T^2$ is $SO_2$:

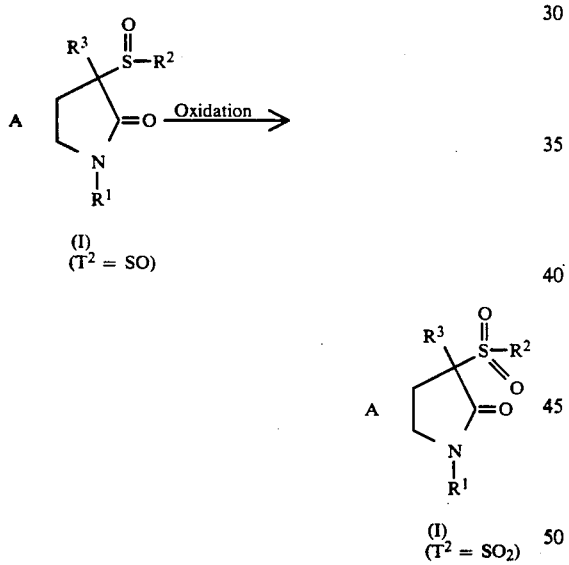

Compounds(I) wherein $T^2$ is SO are treated with a suitable oxidizing agent for oxidizing SO to $SO_2$, such as for example, m-chloroperoxybenzoic acid, hydrogen peroxide, sodium perborate, potassium permanganate and the like. The solvent employed will vary, depending upon the oxidation agent. Representative solvents include the chlorinated hydrocarbons such as dichloromethane, 1,2-dichloroethane, chloroform and the like; and can include protic solvents such as water, methanol or ethanol. The reaction can be carried out at a temperature ranging from about 25° C. to about 60° C. to give compound (I) wherein $T^2=SO_2$.

M. Preparation of compounds wherein $T^2$ is S, and a single bond is at the 2-position:

Compound (I) wherein $T^2=S$ is first treated with a base such as potassium hydride or potassium diisopropylamide in a polar aprotic solvent (such as N,N-dimethylformamide, N,N-dimethylacetamide and the like) at temperatures ranging from about −78° C. to about 0° C. under an inert atmosphere as provided by nitrogen or helium gases. The treatment is followed by addition of $R^{10}L$ wherein L represents a suitable leaving group, such as for example, chloride, bromide, iodide, mesylate, tosylate and the like to give compound (I) having a single bond at the 2-position.

N. Preparation of compounds of formula (II):

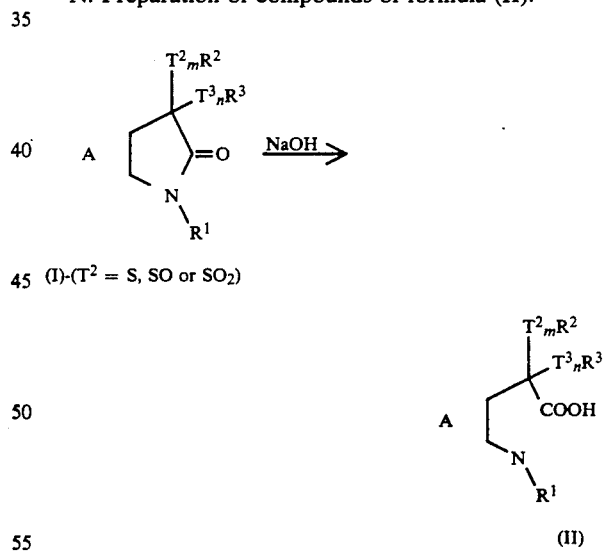

The compounds of formula (II) can be prepared by treating the compounds of formula (I) wherein $T^2$ is S, SO or $SO_2$ with a strong base such as sodium hydroxide, in the presence of any suitable solvent at temperatures in the range of reflux, for example 60° to 100° C. Suitable solvents include protic solvents such as methanol, ethanol and the like.

The compounds of formulas I and II may be prepared by the following processes as follows.

A. To prepare a compound of formula I wherein $R^2$ and $R^3$ are the same and $T^2$ and $T^3$ are not present (i.e. are absent).

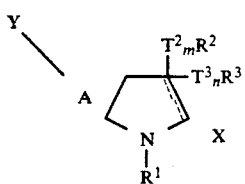

(I)

react a compound of the formula:

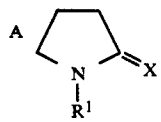

(III)

wherein ring A, X and R¹ are as defined hereinbefore with a compound of the formula

R²L wherein L represents a good leaving group such as chloride, bromide, iodide, mesylate, tosylate, and R² is as defined hereinbefore in the presence of an inert solvent to give the compound of formula I;

B. To prepare the compounds of formula I wherein R² and R³ are the same or different and T² and T³ are not present, react a compound of the formula:

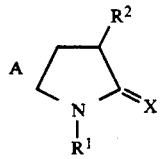

(IV)

wherein ring A, R¹, R² and X are defined hereinbefore with a compound R³L wherein R³ is as defined hereinbefore and L is a leaving group under the same conditions as in process A to give the compound of formula I;

C. To prepare a compound of formula (I) wherein T² and T³ are not present and X is O, react the acid of the formula (V)

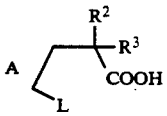

(V)

or a reactive derivative thereof with a suitable condensation agent of the formula R¹NH₂ wherein R¹ is as defined hereinbefore in the presence of an inert solvent to give the compound of formula I;

D. To prepare the compounds of formula I wherein T² and T³ are not present and X is O, react a compound of the formula

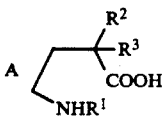

(VI)

with an activating agent such as acetic acid, trifluoroacetic acid or propionic acid or a dehydrating agent such as dicyclohexylcarbodiimide or 1-ethyl-3-(3-dimethylaminopropyl)-carbodiimide in an inert solvent to give the compound of formula I;

E. To prepare the compounds of formula I wherein T² and T³ are not present and X=S, react a compound of the formula:

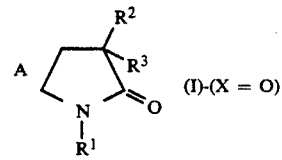

(I)-(X = O)

wherein ring A, R¹, R² and R³ are as defined hereinbefore with a suitable sulfurylating agent in a suitable solvent to give the compound of formula I;

F. To prepare a compound of formula I wherein R¹ represents alkyl and T² and T³ are not present, react a compound of the formula:

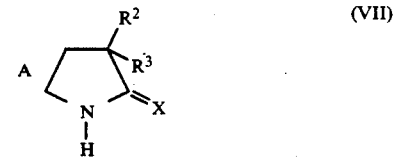

(VII)

wherein ring A, X, R² and R³ are as defined hereinbefore with a base and thereafter adding the alkylating reagent LR¹ wherein L and R¹ are as defined hereinbefore to give the compound of formula I;

G. To prepare the compounds of formula I wherein R¹, R² and R³ are all the same alkyl group, react a compound of the formula:

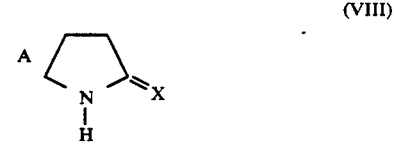

(VIII)

wherein ring A and X are as defined hereinbefore with the alkylating agent LR² wherein R¹=R²=R³=alkyl and L is a leaving group as defined hereinbefore to give the compound of formula I;

H. To prepare compounds of formula I wherein T² is S, react a compound of the formula:

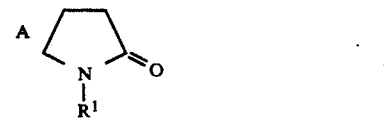

(III)

with N-chlorosuccinimide (NCS) and a suitable sulfide in a suitable solvent to give the compound (I)(f) wherein T² is S

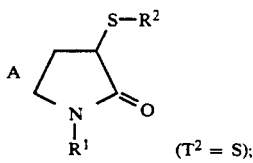

(I)(f)

I. To prepare compounds of formula I wherein $T^2=T^3=S$ and $R^2$ is different from $R^3$, react a compound of the formula:

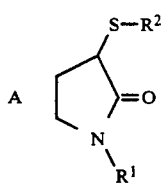

(f)

with N-chlorosuccinimide (NCS) and a suitable sulfide in a suitable solvent to give the compound of the formula I:

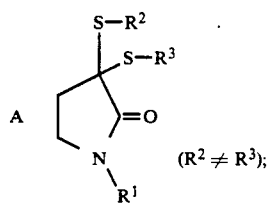

(I)

$(R^2 \neq R^3)$;

J. To prepare compounds wherein $T^2=T^3=S$ and $R^2=R^3$, react a compound of the formula:

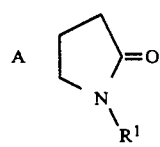

(III)

with N-chlorosuccinimide (NCS) and a suitable sulfide in a suitable solvent to give the compound of the formula:

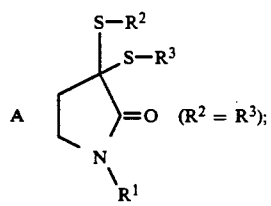

(I)   $(R^2 = R^3)$;

K. To prepare a compound of formula I wherein $T^2$ is SO, react a compound of the formula:

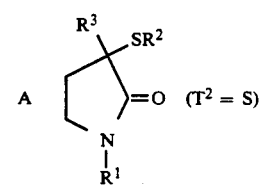

(I)

with any suitable oxidizing agent to oxidize S to SO to give compound (I) wherein $T^2$ is SO:

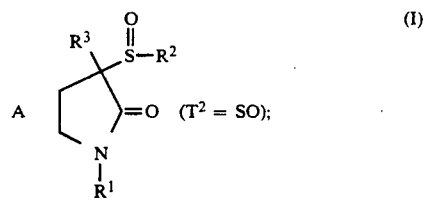

($T^2$ = SO);

L. To prepare a compound of formula I wherein $T^2$ is $SO_2$ react a compound of the formula:

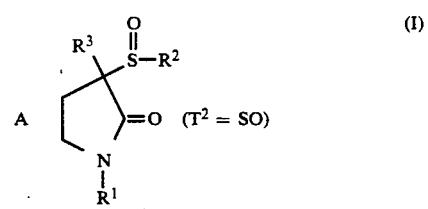

($T^2$ = SO)

with a suitable oxidizing agent for oxidizing SO to $SO_2$ to give compound (I) wherein $T^2=SO_2$ of the formula:

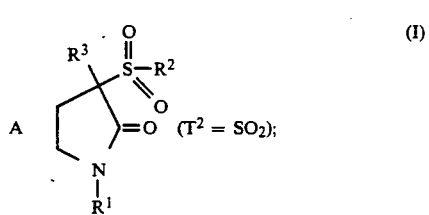

($T^2 = SO_2$);

M. To prepare compounds of formula I wherein $T^2$ is S, and a single bond is at the 2-position, react a compound of the formula:

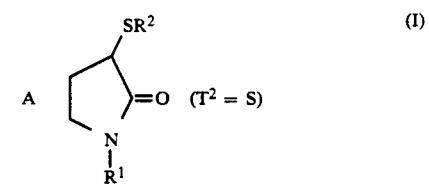

($T^2$ = S)

with a base, followed by addition of $R^{10}L$ wherein $R^{10}$ represents alkyl or aralkyl and L represents a suitable leaving group as defined hereinbefore to give compound (I) having a single bond at the 2-position of the formula

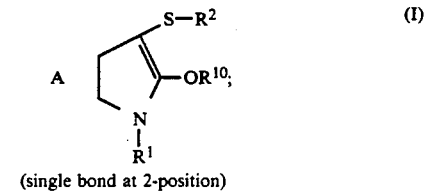

(single bond at 2-position)

N. To prepare compounds of formula (II) react a compound of the formula:

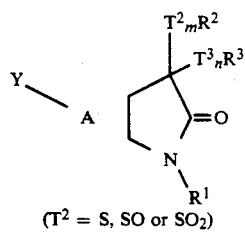

with a strong base such as sodium hydroxide, in the presence of a suitable solvent to give a compound of formula (II):

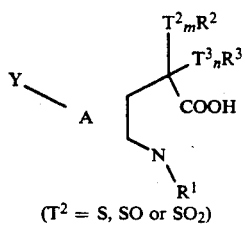

As is apparent to one skilled in the art, depending on substituents already present in the molecule (e.g. different Y substituents), one or more such substituents may have to be protected during some of the reactions A to N above. It is also readily apparent that, subsequent to the above reactions, certain final compounds can be transformed into other final compounds by trivial reactions well-known in the art. For example, if Y represents —S-(lower alkyl), this substituent can be oxidized to —SO-(lower alkyl) and —SO$_2$-(lower alkyl); hydroxy groups can be transformed into an alkoxy-, acyloxy-, alkenyloxy- or alkynyloxy- group; primary amino groups can be transformed into —NHR$^4$ or —N(R$^4$)$_2$; and so on.

The starting compounds II to VIII used in the above processes are either known or they may be prepared according to processes well-known in the art.

Thus, for example, the starting compounds of formula III may be prepared according to the following reaction scheme:

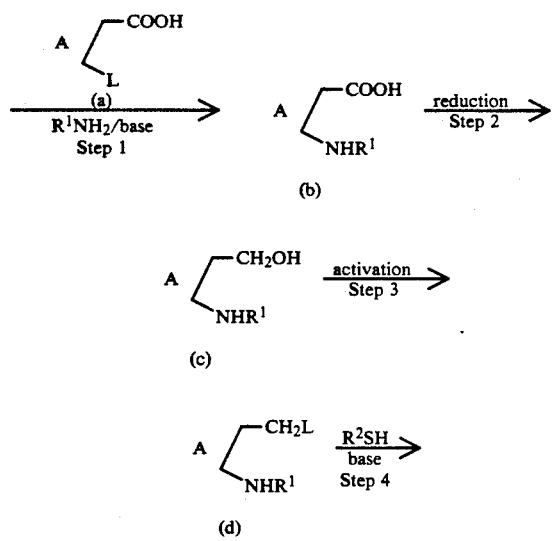

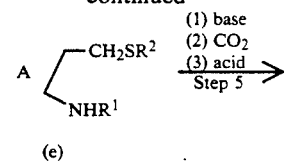

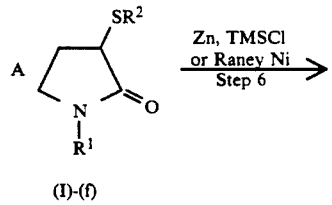

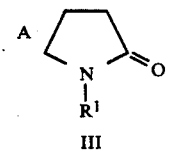

In the above formulae, A, R$^1$, R$^2$ and L are as defined hereinbefore.

Step 1: The preferred leaving groups are chlorine, bromine, mesylate and tosylate and any suitable base such as pyridine or a tertiary amine can be used. Preferably the reaction is carried out in a protic high boiling solvent such as water, pentanol and hexanol and the reaction temperature used depends on this solvent (for the above solvents: 100°–150° C.).

Step 2: Any suitable reduction agent for reducing CO to CH$_2$ can be used, e.g. lithium aluminum hydride, diisobutylaluminum hydride, borane, aluminum hydride, etc. Ethers, tetrahydrofuran and dioxane are preferred solvents. Reaction proceeds at 0° C. to 60° C.

Step 3: The activation means replacing the OH group by a reactive leaving group and accordingly the activating agent used depends on the desired leaving group. Typical examples are thionyl chloride, phosphorus trichloride, phosphorus oxychloride, oxalyl chloride, mesyl chloride and tosyl chloride. Suitable solvents are chlorinated hydrocarbons (e.g. dichloromethane, 1,2-dichloroethane, chloroform) or ethers, tetrahydrofuran and dioxane. Preferred temperature range is 0° C. to 25° C.

Step 4: Alkali metal salts of the lower alkanoates or alkali metal hydroxides are the preferred bases, e.g. sodium methoxide, sodium ethoxide, sodium hydroxide. The reaction is usually carried out in a protic solvent (e.g. water, methanol, ethanol) at temperatures between 0° C. and 25° C.

Step 5: Compound (e) is first treated with a base such as n-butyl lithium or sec-butyl lithium in a solvent (e.g. diethyl ether, tetrahydrofuran or dioxane) at lower temperature, e.g. −78° C. to 0° C. The mixture is treated with CO$_2$ and then the acid is added. Any suitable acid can be used, e.g. acetic acid, trifluoroacetic acid, propionic acid and the like.

Step 6: Starting compounds III is obtained by eliminating the SPh-group from the compound (I)–(f). This is preferably achieved by treating (I)–(f) with Zn and trimethylsilyl-chloride (TMSCl) or with Raney nickel in a suitable solvent such as an ether (diethyl ether), tetrahydrofuran or dioxane at room temperature.

The starting compounds of formula IV may be obtained by first treating compound (I)-(f) above with the alkylating or halogenating reagent ($R^2L$ or $R^3L$), followed by elimination of the $-SR^2$ group:

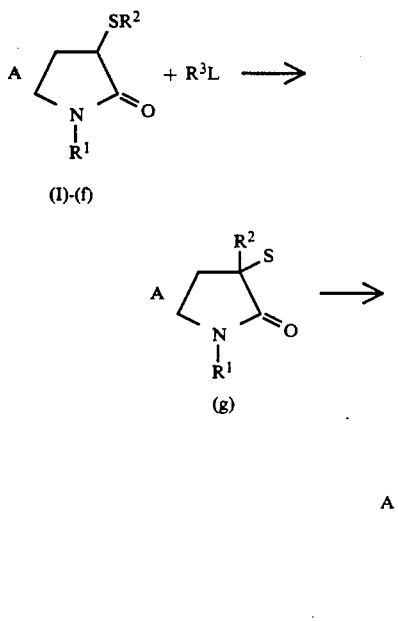

The conditions and reagents for introducing the $R^2$ group and for the elimination of $-SR^2$ may be the same as those used in process A and in Step 6 above, respectively.

Starting compounds of formula V may be prepared according to the following reaction steps:

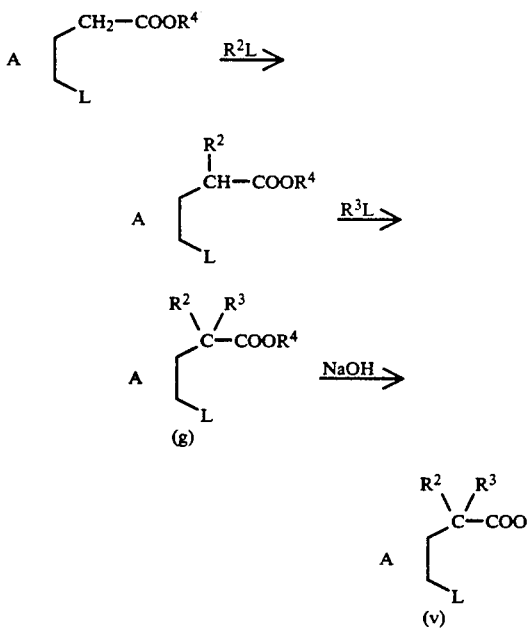

The introduction of $R^2$ and $R^3$ may be achieved by using reagents and conditions as defined for process A. $R^4$ is alkyl such as ethyl. The last step is a simple hydrolysis of the ester with a base.

Starting compounds of formula VI are conveniently prepared by reacting compound (g) above with $R^1NH_2$ in the presence of a base (e.g., pyridine or a tertiary amine such as trimethylamine, triethylamine, tributylamine, N-methylmorpholine, N-methylpiperidine) in a high boiling protic solvent (e.g., water, pentanol, hexanol, etc.) at elevated temperature (reflux).

Compounds of formula VII are either known compounds or may be obtained by introducing $R^2$ and $R^3$ into a compound of the formula

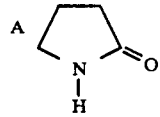

(J. Am. Chem. Soc., 81, 740 (1953) and J. Org. Chem., 48, 3401 (1983)) according to procedures described above.

The compounds of formula I or II wherein $T^2$ and $T^3$ are not present (i.e. absent) where m and n are zero, inhibit the formation of both 5-lipoxygenase (5-LO) and cyclooxygenase (CO) derived products of arachidonic acid metabolism. The compounds of the invention may thus be used to treat arthristis, bursitis, tendonitis, gout and other inflammatory or hyperproliferative conditions of the skin (i.e. eczemas or psoriasis) and other organs (i.e. bowel diseases). Such compounds can also be used to treat allergic conditions such as allergic rhinitis or coryza, hay fever, bronchial asthma and urticria(-hives).

The biological activity of classical nonsteroidal antiiflammatory drugs (NSAID) is attributable to inhibition of the cyclooxygenase pathway which converts arachidonic acid to prostaglandins. In diseases such as rheumatoid arthritis, the NSAIDs have limited efficacy since the cause of rheumatoid arthritis involves more than one mechanism. This hypothesis has been supported by the discovery of proinflammatory leukotrienes including a chemoattractant for neutrophils, leukotriene B4, which is formed from arachidionic acid via the 5-lipoxygenase pathway. Therefore, a drug that inhibits both the cyclooxygenase and 5-lipoxygenase pathways may be a superior antiinflammatory agent for particular applications relative to one that inhibits only one of these pathways. Alternatively, the sulfur containing compounds of formulas I and II wherein $T^2$ or $T^3$ is S, SO or $SO_2$ inhibit primarily the 5-LO derived products of arachidonic acid metabolism. Such compounds may be more useful for topical applications, such as for treating inflammatory skin diseases. Such compounds are also useful for treating allergic conditions such as those described hereinabove.

Reversed Passive Arthus Reaction (RPAR) Assay

The 5-LO and CO inhibition of the compounds of the invention may be demonstrated by the Reversed Passive Arthus Reaction (RPAR) in the pleural cavity by the procedure described below:

Groups of 4 male rats were injected in the penile vein with antigen (1 mg BSA in 0.2 mL of saline per rat) and 0.5 hour later injected in the pleural cavity with antibody (1.0 mg antibody protein in the IgG fraction of rabbit anti-BSA in 0.2 mL). Sham control animals were treated as RPAR animals but did not receive BSA antigen. After 4 hours the animals were killed with $CO_2$, and the pleural cavities were opened and the exudate drained into a graduated conical glass centrifuge tube containing indomethacin (1.8 ug) and nordihydroguaiaretic acid (NDGA) (15 ug) to block ex vivo metabolite synthesis. The volume of the exudate was measured. The cavity was then washed out with saline-EDTA to achieve a final volume of 5.0 mL. The number of cells were determined in a Colulter Counter. The cells were spun-down (1000×g) and the exudate supernatant was added to 4 volumes of 95% ethanol and samples were kept on ice for 30 minutes. After removal of the protein precipitate (2,500×g) the ethanol extract of the exudate was dried under $N_2$ and then stored at $-20°$ C. For radioimmunoassay (RIA) analysis the samples were redissolved in water to a volume of 1 mL per rat. Utilizing internally spiked samples, recovery of $TXB_2$ (tritiated thromboxane $B_2$) and $LTE_4$ (tritiated leukotriene-$E_4$) from exudates was determined to be 84±2% (SEM) and 89±2% (N=4), respectively. Exudate samples were directly assayed in duplicate with the commercial $^3H$-$TXB_2$ RIA kit from New England Nuclear and the $^3H$-$LTC_4/D_4/E_4$ kit from Amersham. The assay was validated using reversed-phase HPLC analysis of LTs in the standard procedure described by M. W. Musch, R. W. Bryant, C. Coscollaela, R. F. Myers and M. I. Siegel, *Prostaglandins*, Vol. 29, pp 405-430 (1985). Samples of ethanol exudate extract were "spiked" with $^3H$-LTs to follow HPLC purification and recovery.

As is normal with inventions of this type, some compounds are more active than others. The following Table 1 shows the activity of a representative selection of compounds of formula (I).

5-Lipoxygenase Assay

Human polymorphonuclear (PMN) leukocytes (neutrophils) are obtained from normal healthy volunteers by venipuncture and collected with heparin anticoagulant. Neutrophils are isolated by Dextran/Ficol sedimentation as described (Billah et al, *J. Biol. Chem.* 260, 6899-6906 (1985)). In brief, 30 ml of blood is mixed with 5 ml of dextran (Sigma) solution and kept at 37° C. for 30 min. The upper white cellrich layer is removed and 10 ml is layered on 9 ml of Ficol-Paque solution (Pharmacia) and centrifuged at 280×g for 10 min. at 5° C. The supernatant is removed and the neutrophil pellet is resuspended in HEPES buffer containing 25 mM N-2-hydroxyethylpiperazine-$N^1$-2 ethanesulfonic acid(-HEPES), 125 mM NaCl, 2.5 mM KCL, 0.7 mM $MgCl_2$, 0.5 mM and 10 mM glucose at pH 7.4. The red cells in the suspension are lysed by hypotonic shock. The neutrophils are washed by centrifugation in HEPES buffer two times and finally resuspended at a concentration of $20\times10^6$ cells/ml in the presence of 1 mM $CaCl_2$.

TABLE 1

(Iiv)

| Compound No. | $R^1$ | $R^2$ | $R^3$ | X | Dose (mpk) | % Inhibition cells | % Inhibition fluid | LTE-4 | TXB-2 |
|---|---|---|---|---|---|---|---|---|---|
| 1 | phenyl | $CH_3$ | $CH_3$ | O | 40 | 70 | 60 | 54 | 54 |
| 2 | 4-chlorophenyl | $CH_3$ | $CH_3$ | O | 25 | 73 | 83 | 87 | 78 |
| 3 | methyl | $CH_3$ | $CH_3$ | O | 25 | 69 | 53 | 62 | 17 |
| 4 | phenyl | $CH_3$ | F | O | 25 | 50 | 35 | N.T. | N.T. |
| 5 | 3-chlorophenyl | $CH_3$ | $CH_3$ | O | 25 | 51 | 49 | 59 | 62 |
| 6 | 3,4-dichlorophenyl | $CH_3$ | $CH_3$ | O | 25 | 26 | 25 | 46 | 44 |
| 7 | phenyl | $CH_3$ | $CH_3$ | S | 25 | 35 | 33 | N.T. | N.T. |
| 8 | 4-methoxyphenyl | $CH_3$ | $CH_3$ | O | 25 | 63 | 42 | 0 | 34 |
| 9 | 4-fluorophenyl | $CH_3$ | $CH_3$ | O | 20 | 70 | 43 | 36 | 53 |
| 10 | 4-methylthiophenyl | $CH_3$ | $CH_3$ | O | 25 | 29 | 37 | N.T. | N.T. |

N.T. = NOT TESTED

TABLE 1A

| Compound No. | Compound Name |
|---|---|
| 1 | 1,3-dihydro-3,3-dimethyl-1-phenyl-2H-pyrrolo[2,3-b]pyridin-2-one, |
| 2 | 1-(4-chlorophenyl)-1,3-dihydro-3,3-dimethyl-2H-pyrrolo[2,3-b]pyridin-2-one, |
| 3 | 1,3-dihydro-1,3,3-trimethyl-2H-pyrrolo[2,3-b]pyridin-2-one, |
| 4 | 1,3-dihydro-3-fluoro-3-methyl-1-phenyl-2H-pyrrolo[2,3-b]pyridin-2-one |
| 5 | 1-(3-chlorophenyl)-1,3-dihydro-3,3-dimethyl-2H-pyrrolo[2,3-b]pyridin-2-one, |
| 6 | 1-(3,4-dichlorophenyl)-1,3-dihydro-3,3-dimethyl-2H-pyrrolo[2,3-b]pyridin-2-one, |
| 7 | 1,3-dihydro-3,3-dimethyl-1-phenyl-2H-pyrrolo[2,3-b]pyridin-2-thione |
| 8 | 1,3-dihydro-3,3-dimethyl-1-(4-methoxyphenyl)-2H-pyrrolo[2,3-b]pyridin-2-one |
| 9 | 1,3-dihydro-3,3-dimethyl-1-(4-fluorophenyl)-2H-pyrrolo[2,3-b]pyridin-2-one, |
| 10 | 1,3-dihydro-3,3-dimethyl-1-[4-(methylthio)phenyl]-2H-pyrrolo[2,3-b]pyridin-2-one |

Neutrophils (0.2 ml of suspension) are preincubated with dimethylsulfoxide (DMSO) vehicle with or without test compound (1 ul) for 4 minutes then incubated for 5 minutes with $^{14}C$-arachidonic acid (Amersham, 59 Ci/mole) at a 9 uM final concentration, and the calcium ionophore A23187 (Calbiochem) at a 1 uM final concentration. These stimulants are added in 10 ul of water:ethanol (9:1). The reaction is stopped by addition of methanol (0.4 ml), and cellular debris is removed by centrifugation. Aliquots (100 ul) of the incubations are run on a Waters two pump high performance liquid chromatography (HPLC) system fitted with a DuPont Zorbax ODS, 5 u, 4×80 cm Reliance Cartridge column and C18 "Guard Pak". The column is initially eluted at 2 ml/min with 80 percent of the mixture water:methanol:acetic acid (46:54:0.08) containing 1 mM EDTA adjusted to pH 6.0 with ammonium hydroxide (Pump A) and 20% methanol (Pump B). At 10 minutes, a linear gradient is established to reach 100 percent methanol (Pump B) at 27 minutes. Between 27 and 28 minutes, methanol is exchanged for the initial eluting solvent and by 35 minutes the column is reequilibrated for the next sample. The effluent is analyzed by a continuous flow radioactivity monitor (model ROMONA-D) interfaced with a Hewlett Packard Lab Automation System for quantitation of radioactive products. This includes the major 5-lipoxygenase product, 5-hydroxyeicosatetraenoic acid (5-HETE) which elutes at 20 minutes. The results with and without test compound are used to calculate percent inhibition of 5-HETE production.

Cyclooxygenase Assay with Human Platelets

Blood is collected in acid-citrate-dextrose anticoagulant by venipuncture from normal healthy volunteers who said that they were not on any medication for the previous two weeks. Platelets are isolated by the procedure of Okuma and Uchino (Blood 54:1258–1271 (1979)). In brief, blood is centrifuged at 4° C. at 200×g for 10 minutes to sediment red and white cells. The platelet rich plasma (PRP) supernatant is removed and mixed with one-tenth volume of 77 mM EDTA, pH 7.2 and prostacyclin sodium salt is added to the PRP at a final concentration of 1 nanogram per milliliter(ng/mL). The PRP is centrifuged at 1700×g, 4° C. for 15 minutes. The platelet pellet is resuspended in the HEPES buffer described in the 5-lipoxygenase section above which additionally contained 1 ng/mL prostacyclin and 0.5 mM ethylene glycolbis(B-aminoethyl ether) N,N,N',N'-tetraacetic acid (EGTA) and the suspension is recentrifuged at 1,700×g, 4° C. for 15 minutes. The pellet is resuspended in HEPES buffer containing 0.5 mM EGTA and 1.5 mM $CaCl_2$ at a cell count of 200,000 cells/ul. Platelets (0.2 ml of suspension) are preincubated with test compounds and the $^{14}$C-arachidonic acid plus the calcium ionophore A23187 stimulant exactly as described for the 5-lipoxygenase assay. The cyclooxygenase product 12-hydroxyheptadecatrienoic acid (HHT) is isolated and quantitated by the HPLC system used for the 5-lipoxygenase assay. HHT elutes from this system at about eleven minutes. Results are expressed as percent inhibition of HHT production by the test compounds versus the test vehicle alone.

As is normal with inventions of this type, some compounds are more active than others. In Table 2 is shown the activity of a representative selection of compounds of formula (I).

TABLE 2

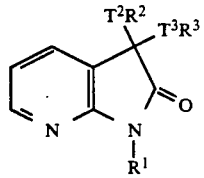

(Iv)

| Compound No. | $R^1$ | $T^2$ | $R^2$ | $T^3$ | $R^3$ | Dose (μM) | PMN Assay % Inhibition HHT | 5-HETE |
|---|---|---|---|---|---|---|---|---|
| 11 | phenyl | S | phenyl | — | H | 15 | 23 | 67 |
| 12 | 3-$CF_3$ phenyl | S | phenyl | — | H | 15 | N.T. | 79 |
| 13 | 3-$CF_3$-phenyl | SO | phenyl | — | H | 50 | 44 | 82 |
| 14 | isopropyl | S | phenyl | — | H | 50 | 17 | 63 |
| 15 | 4-isopropyl-phenyl | S | phenyl | — | H | 50 | N.T. | 84 |
| 16 | phenyl | S | phenyl | — | $CH_3$ | 50 | 2 | 68 |
| 17 | methyl | S | phenyl | — | H | 50 | 21 | 63 |
| 18 | 2-methyl-3 Cl-phenyl | S | phenyl | — | H | 50 | 64 | 86 |
| 19 | phenyl | S | 4-Cl-phenyl | — | H | 50 | 71 | 91 |
| 20 | phenyl | S | 2-Cl-phenyl | — | H | 50 | 80 | 90 |
| 21 | phenyl | S | 4-methoxyphenyl | — | H | 15 | N.T. | 61 |
| 22 | phenyl | S | 2-methoxyphenyl | — | H | 50 | 31 | 84 |
| 23 | phenyl | S | 2-methylphenyl | — | H | 50 | N.T. | 81 |
|  |  |  |  |  |  | 15 | 49 | 47 |
| 24 | methyl | SO | phenyl | — | H | 15 | N.T. | 24 |
| 25 | phenyl | S | —$(CH_2)_2$OH | — | H | 15 | N.T. | 8 |
| 26 | —$CH_2$-phenyl | S | phenyl | S | phenyl | 15 | 11 | 96 |
| 27 | —$CH_2$-phenyl | S | phenyl | — | H | 15 | N.T. | 16 |
| 28 | phenyl | S | —$(CH_2)_2$OCO$CH_3$ | — | —CO$CH_3$ | 15 | 35 | 80 |
|  |  |  |  |  |  | 15 | 29 | 96 |
| 29 | phenyl | S | —$(CH_2)_2$OH— | — | —CO$CH_3$ | 15 | N.T. | 56 |
| 30 | phenyl | S | —$(CH_2)_2$OCO$CH_3$ | — | — | 15 | N.T. | 26 |
| 31 | methyl | $SO_2$ | phenyl | — | H | 15 | N.T. | 10 |
| 32 | phenyl | S | methyl | — | methyl | 15 | N.T. | 21 |
| 33 | 3-Cl-phenyl | S | phenyl | — | H | 15 | 52 | 87 |
| 34 | 3,4-dichlorophenyl | S | phenyl | — | H | 15 | 54 | 99 |

N.T. = NOT TESTED

Compound No. 35, wherein for Formula (Iiii), $Y^1$ is H, $R^1$ is phenyl, $T^2$ is S and $R^{10}$ is methyl, otherwise known as 2-methoxy-1-phenyl-3-(phenylthio)-1H-pyrrolo[2,3-b]pyridine exhibits in the PMN assay a 55 percent inhibition of HHT and an 80 percent inhibition of 5-HETE.

The names of compounds 11–34 are provided in Table 2A below:

TABLE 2A

| Compound No. | Compound Name |
|---|---|
| 11 | 1,3-dihydro-1-phenyl-3-(phenylthio)-2H-pyrrolo[2,3-b]pyridin-2-one |
| 12 | 1,3-dihydro-3-(phenylthio)-1-(3-trifluoromethylphenyl)-2H-pyrrolo[2,3-b]pyridin-2-one |
| 13 | 1,3-dihydro-3-(phenylsulfinyl)-1-(3-trifluoromethylphenyl)-2H-pyrrolo[2,3- |

TABLE 2A-continued

| Compound No. | Compound Name |
|---|---|
| | b]pyridin-2-one |
| 14 | 1,3-dihydro-1-(methylethyl)-3-(phenylthio)-2H-pyrrolo[2,3-b]pyridin-2-one |
| 15 | 1,3-dihydro-1-(4-(1-methylethyl)-phenyl)-3-(phenylthio)-2H-pyrrolo[2,3-b]pyridin-2-one |
| 16 | 1,3-dihydro-3-methyl-1-phenyl-3-(phenylthio)-2H-pyrrolo[2,3-b]pyridin-2-one |
| 17 | 1,3-dihydro-1-methyl-3-(phenylthio)-2H-pyrrolo[2,3-b]pyridin-2-one |
| 18 | 1,3-dihydro-1-(3-chloro-2-methylphenyl)-3-(phenylthio)-2H-pyrrolo[2,3-b]pyridin-2-one |
| 19 | 1,3-dihydro-3-(4-chlorophenylthio)-1-phenyl-2H-pyrrolo[2,3-b]pyridin-2-one |
| 20 | 1,3-dihydro-3-(2-chlorophenylthio)-1-phenyl-2H-pyrrolo[2,3-b]pyridin-2-one |
| 21 | 1,3-dihydro-3-(4-methoxyphenylthio)-1-phenyl-2H-pyrrolo[2,3-b]pyridin-2-one |
| 22 | 1,3-dihydro-3-(2-methoxyphenylthio)-1-phenyl-2H-pyrrolo[2,3-b]pyridin-2-one |
| 23 | 1,3-dihydro-3-(2-methoxyphenylthio)-1-phenyl-2H-pyrrolo[2,3-b]pyridin-2-one |
| 24 | 1,3-dihydro-1-methyl-3-(phenylsulfinyl)-2H-pyrrolo[2,3-b]pyridin-2-one |
| 25 | 1,3-dihydro-3-(2-hydroxyethylthio)-1-phenyl-2H-pyrrolo[2,3-b]pyridin-2-one |
| 26 | 1,3-dihydro-3,3-(diphenylthio)-1-(phenylmethyl)-2H-pyrrolo[2,3-b]pyridin-2-one |
| 27 | 1,3-dihydro-1-(phenylmethyl)-3-(phenylthio)-2H-pyrrolo[2,3-b]pyridin-2-one |
| 28 | 1,3-dihydro-3-[2-(acetoxy)-ethylthio]-3-(1-oxoethyl)-1-phenyl-2H-pyrrolo[2,3-b]pyridin-2-one |
| 29 | 1,3-dihydro-3-[2-(hydroxyethylthio]-3-(1-oxoethyl)-1-phenyl-2H-pyrrolo[2,3-b]pyridin-2-one |
| 30 | 1,3-dihydro-3-[2-(acetoxy)-ethylthio]-1-phenyl-2H-pyrrolo[2,3-b]pyridin-2-one |
| 31 | 1,3-dihydro-1-methyl-3-(phenylsulfonyl)-2H-pyrrolo[2,3-b]pyridin-2-one |
| 32 | 1,3-dihydro-3-methyl-3-(methylthio)-1-phenyl-2H-pyrrolo[2,3-b]pyridin-2-one |
| 33 | 1,3-dihydro-1-(3-chlorophenyl)-3-(phenylthio)-2H-pyrrolo |
| 34 | 1,3-dihydro-1-(3,4-dichlorophenyl)-3-(phenylthio)[2,3-b]pyridin-2-one. |

As is normal with inventions of this type, some compounds are more active than others. The following Tables 3A and 3B show the biological activities and melting points of a representative selection of compounds of formula (II).

TABLE 3A

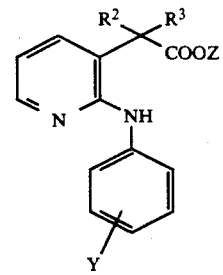

(IIi)

| Compound No. | R² | R³ | Y | Z | Dose (mpk) | RPAR-Pleural Cavity Percent Inhibition | |
|---|---|---|---|---|---|---|---|
| | | | | | | cells | fluid |
| 45 | H | H | 3-CF₃ | H | 25 | 22 | 14 |
| 46 | methyl | methyl | 4-Cl | Na | 25 | 62 | 71 |
| 47 | H | H | 3,4-dichloro | Na | 25 | 16 | 19 |

TABLE 3A-continued

| | | | | | | | |
|---|---|---|---|---|---|---|---|
| 48 | H | H | 4-Cl | Na | 25 | 0 | 0 |
| 49 | methyl | H | 4-Cl | Na | 25 | 67 | 54 |

TABLE 3B (IIi)

| Compound No. | R² | R³ | Y | Z | m.p. (°C). if solid |
|---|---|---|---|---|---|
| 45 | H | H | 3-CF₃ | H | 173–174 |
| 46 | methyl | methyl | 4-Cl | Na | 240–245 |
| 47 | H | H | 3,4-dichloro | Na | 90–100 |
| 48 | H | H | 4-Cl | Na | 150–160 |
| 49 | methyl | H | 4-Cl | Na | 160–170 |

The names of compounds 45–49 are provided in Table 3C.

TABLE 3C

| Compound No. | Compound Name |
|---|---|
| 45 | 2-(3-trifluoromethylphenylamino)-3-pyridine acetic acid |
| 46 | sodium 2-(4-chlorophenylamino)-α,α-dimethyl-3-pyridine acetate |
| 47 | sodium 2-(3,4-dichlorophenylamino)-3-pyridine acetate |
| 48 | sodium 2-(4-chlorophenylamino)-3-pyridine acetate |
| 49 | sodium 2-(4-chlorophenylamino)-α-methyl-3-pyridine acetate |

The compounds of formulas I and II can be administered in any number of conventional dosage forms. Solid dosage forms include capsules, tablets, pills, powders, suspensions, solutions, cachets or suppositories. Parenteral preparations include sterile solutions or suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, blinders, flavorings, buffers, thickeners, color agents, stabilizing agents, perfumes, preservatives, lubricants, etc.

When used orally or parenterally for the treatment of inflammation, the compounds of the invention can be administered in an amount ranging from about 0.1 mg/kg to about 100 mg/kg, preferably from 0.1 mg/kg to about 25 mg/kg per day. Determination of the proper dosage of a compound of the invention for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if required.

The amount and frequency of administration of the compounds of formulas I and II and the pharmaceutically acceptable salts thereof will be regulated according to the judgment of the attending clinician considering such factors as age, condition and size of patient as well as severity of the symptom being treated. A typical recommended dosage regimen is oral administration of from 10 mg to 1500 mg/day preferably 10 to 750 mg/day, in two to four divided doses to achieve relief of the inflammation symptoms.

The following examples are intended to illustrate methods for preparing the compounds of the present invention as well as starting materials therefor, but should not be considered limited to the specific examples provided.

PREPARATION OF STARTING MATERIALS

A:
1-(4-Chlorophenyl)-1,3-dihydro-2H-pyrrolo-(2,3-b)pyridin-2-one

Step 1: 2-[(4-Chloropheyl)amino]-3-pyridinecarboxylic acid

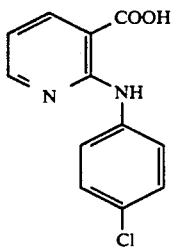

Reflux a mixture of 4-chloroaniline (81.2 g, 0.636 mole), 2-chloro-3-pyridinecarboxylic acid (91.4 g, 0.58 mole), pyridine (50.4 g, 0.636 mole) and p-toluenesulfonic acid (8.0 g) in water (500 mL) for 6 hours. Cool to room temperature and filter. Wash the filter cake with water and diethyl ether. Dry the solid to give the title compound (A) as a yellow solid (118 g, m.p. 205°-207° C.).

Step 2: 2-[(4-Chlorophenyl)amino]-3-pyridinemethanol (Compound B)

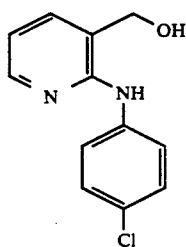

Add 2-[(4-chlorophenyl)amino]-3-pyridinecarboxylic acid (A) (118 g, 0.47 mole) portionwise to a paddle stirred suspension of lithium aluminum hydride (36.8 g, 0.96 mole) in diethyl ether (2600 mL). Reflux the reaction mixture for 24 hours, and then cool to room temperature. Add dropwise in sequence water (37 mL), 20% aqueous NaOH (37 mL), and water (48 mL). Filter the suspension, and wash the filter cake with dichloromethane. Rotoevaporate the filtrate to give a solid. Triturate the solid with petroleum ether and filter to give the title compound (B) as a white solid (107.1 g, m.p. 119°-122° C.).

Step 3:

3-(Chloromethyl)-N-(4-chlorophenyl)-2-pyridinamide, hydrochloride (Compound C)

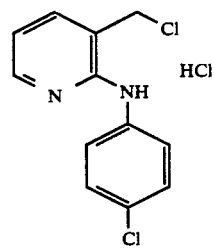

Add thionyl chloride (82.5 mL, 134.5 g, 1.13 mole) to 2-[(4-chlorophenyl)amino]-3-pyridinemethanol (B) in dichloromethane (1500 mL) at 20° C. to 30° C. Stir for 16 hours at room temperature. Filter the suspension, and wash the filter cake with diethyl ether to give the title compound (C) as a light yellow solid (123.9 g, m.p. 193°-195° C.).

Step 4:

N-(4-Chlorophenyl)-3-[(phenylthio)methyl]-2-pyridinamine (Compound D)

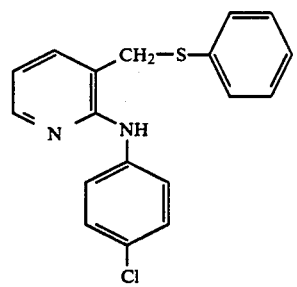

Add thiophenol (50.2 g, 0.546 mole) to a stirred solution of NaOH (40.0 g, 1.0 mole) in water (275 mL) and ethanol (2500 mL). Cool to 5° C., and add portionwise 3-(chloromethyl)-N-(4-chlorophenyl)-2-pyridinamine, hydrochloride (C) (125.7 g, 0.43 mole) (d). Stir for 16 hours at room temperature. Add water (4.0 L), and filter to give a yellow solid. Dissolve the solid in dichloromethane, dry with MgSO$_4$, filter, and rotoevaporate to give the title compound (D) as a yellow solid (138.4 g, m.p. 70°-73° C.).

Step 5:
1-(4-Chlorophenyl)-1,3-dihydro-3-(phenylthio)2H-pyrrolo[2,3-b]pyridin-2-one (Compound E)

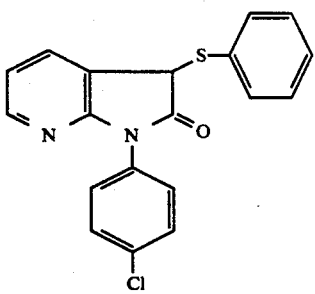

Add n-butyl lithium (183.7 mL, 2.5M in THF) to N-(4-chlorophenyl)-3-[(phenylthio)methyl]-2-pyridinamine (D) (61.5 g, 0.188 mole) in dry THF (600 mL) at −60° C. to −55° C. under a N₂ atmosphere. Stir for 3 hours at −70° C., warm to −30° C. for 15 minutes, and recool to −70° C. Pour the reaction mixture onto a paddle stirred suspension of powdered dry ice (1500 mL) in diethyl ether (2000 mL). Evaporate the solution for 16 hours in the hood to give a solid. Add water (800 mL) and wash with diethyl ether. Acidify the aqueous solution to pH=3 to 4 with 15% aqueous HCl, and extract with dichloromethane. Dry the organic solution with MgSO₄, filter and rotovap to give an oil. Dissolve the oil in dichloromethane (1.0 L), and add trifluoroacetic acid (100 mL). Stir for 16 hours at room temperature. Rotoevaporate the solution to give an oil. Add saturated aqueous NaHCO₃, and extract with dichloromethane. Dry the organic solution with MgSO₄, filter, and rotoevaporate to give an oil. Dissolve the oil in dichloromethane, and chromatograph on silica gel, eluting with dichloromethane. Combine the appropriate fractions, and concentrate under reduced pressure to give the title compound (E) as a white solid (39.8 g, m.p 93°–96° C.).

Step 6:
1-(4-Chlorophenyl)-1,3-dihydro-2H-pyrrolo[2,3-b]-pyridin-2-one (Compound F)

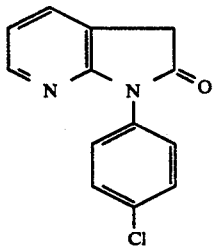

Add trimethylsilylchloride (58.8 g, 0.54 mole) dropwise to 1-(4-chlorophenyl)-1,3-dihydro-3-(phenylthio)-2H-pyrrolo-[2,3-b]pyridin-2-one (E) (28.0 g, 0.079 mole) and zinc dust (26.2 g, 0.40 mole) in THF (350 mL), diethyl ether (170 mL), and water (2.0 mL) at less than 40° C. Stir for 16 hours at room temperature. Rotoevaporate to give an oil, and add dichloromethane (500 mL). Wash the organic solution with 10% aqueous NaOH (300 mL) and water (300 mL). Dry with MgSO₄, filter, and rotoevaporate to give the title compound (F) as a yellow solid (19.6 g, m.p. 148°–150° C.).

By using the methods basically as described above in Steps 1 to 6, the following compounds in Table 4 below may also be prepared:

TABLE 4

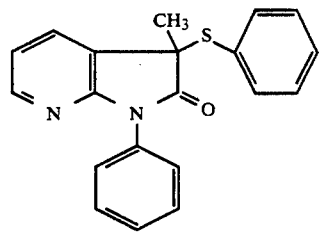

| R¹ | m.p. (°C.). if solid |
|---|---|
| phenyl | 120–121 |
| 4-isopropylphenyl | 78–80 |
| isopropyl | 62–63 |
| 3-chlorophenyl | 143–145 |
| 3,4-dichlorophenyl | 183–184 |
| 4-fluorophenyl | 163–164 |
| 4-methylthiophenyl | 143–145 |
| 3-trifluoromethylphenyl | 128–130 |
| 4-bromophenyl | 130–133 |
| 2,4-dichlorophenyl | 184–185 |
| 2-methyl-3-chlorophenyl | 144–146 |

B:
1,3-Dihydro-3-methyl-1-phenyl-2H-pyrrolo[2,3-b]pyridin-2-one

Step 1:
1,3-Dihydro-3-methyl-1-phenyl-3-(phenylthio)-2H-pyrrolo[2,3-b]pyridin-2-one (Compound G)

Add 1,3-dihydro-1-phenyl-3-(phenylthio)-2H-pyrrolo[2,3-b]pyridin-2-one (13.00 g, 0.0408 mole) portionwise to sodium hydride (1.80 g of 60% NaH in oil, washed with hexane, 44.91 mmole) in dry THF (175 mL) at 0° C. under a N₂ atmosphere. Stir for 30 minutes at room temperature, and then recool to 0° C. Add iodomethane 3.18 mL, 7.24 g, 0.0510 mole) dropwise, and warm reaction mixture up to room temperature slowly. Stir for 16 hours at room temperature. Rotoevaporate to remove the solvent. Add saturated aqueous NaHCO₃ (150 mL), and extract with ethyl acetate. Wash with saturated aqueous NaCl (150 mL), dry the organic solution with MgSO₄, filter and rotoevaporate to give a solid. Recrystallize with isopropyl acetate-isopropyl ether to give the title compound (G) as a yellow solid (11.03 g, m.p.=110°–112° C.).

Step 2:
1,3-Dihydro-3-methyl-1-phenyl-2H-pyrrolo[2,3-b]pyridin-2-one (Compound H)

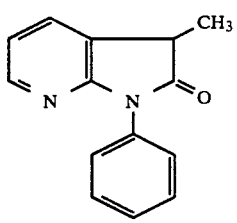

Add trimethylsilylchloride (29.4 mL, 25.21 g, 0.232 mole) to 1,3-dihydro-3-methyl-1-phenyl-3-(phenylthio)-2H-pyrrolo[2,3-b]pyridin-2-one (G) (11.02 g, 0.0331 mole) and zinc dust (10.83 g, 0.166 mole) in THF (200 mL) and water (2.0 mL) dropwise at less than 40° C. Stir for 5 hours at room temperature. Filter to remove zinc, and wash filter cake with dichloromethane. Rotoevaporate filtrate. Add 1N NaOH (60 mL) and saturated aqueous NaHCO3 (150 mL). Extract the aqueous solution with ethyl acetate. Wash the organic solution with saturated NaCl, dry with MgSO4, filter and rotoevaporate to give a yellow oil. Dissolve the oil in dichloromethane, and chromatograph on silica gel, eluting with ethyl acetate:hexane (1:3) then ethyl acetate:hexane (1:1). Combine the appropriate fractions, and concentrate under reduced pressure to give a colorless oil. Crystallize the oil with isopropyl ether-petroleum ether to give the title compound (H) as a white solid (5.60 g, m.p. 60°-63° C.).

C:
1,3-Dihydro-1-(4-methoxyphenyl)-2H-pyrrolo[2,3-b]pyidin-2-one (Compound J)

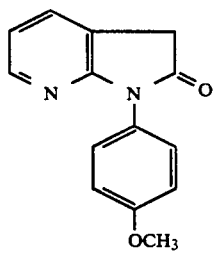

Reflux 2-chloro-3-pyridineacetic acid (4.0 g, 0.0223 mole), p-methoxyaniline (4.6 g, 0.052 mole), and p-toluenesulfonic acid (50 mg) in amyl alcohol (20 mL) for 18 hours. Cool to room temperature. Add water and chloroform:ethyl acetate (1:3 by volume). Separate layers. Dry organic layer with MgSO4, filter and rotoevaporate to give a solid. Triturate with isopropyl ether, and filter to give the title compound (J) as a tan solid (3.7 g, m.p. 138°-140° C.).

Basically the same procedure as described above may be used to synthesize the compounds in Table 5 below:

TABLE 5

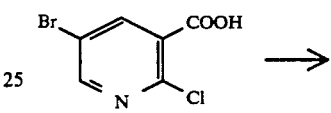

| $R^1$ | m.p. (°C.) (if solid) |
|---|---|
| 2,4-difluorophenyl | 128–129 |
| 3,5-dichlorophenyl | 221–222 |

D:
5-Bromo-2-[(4-chlorophenyl)amino]-a,a-dimethyl-3-pyridineacetic acid

Step 1: (Phenylmethyl) 2-(3-(5-bromo-2-chloro)pyridyl)acetate (Compound K)

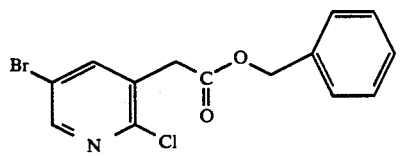

Reflux 5-bromo-2-chloronicotinic acid (25.0 g, 0.106 mole), thionyl chloride (100 mL), and dimethylformamide (1 mL) for 22 hours. Cool to room temperature, filter, and rotoevaporate the filtrate. Add chloroform, and rotoevaporate again to give an orangish-brown solid. Dissolve the solid in THF (150 mL) and acetonitrile (150 mL), and cool to 0° C. under a N2 atmosphere. Add triethylamine (27.4 mL, 19.9 g, 0.196 mole) and then trimethylsilyldiazomethane (108 mL of a 10% by weight solution in dichloromethane, 13.44 g, 0.118 mole) dropwise by addition funnel at less than 10° C. Stir for 5 hours at 0° C., and then warm slowly to room temperature. Stir for 16 hours at room temperature. Rotoevaporate the reaction mixture, add diethyl ether (500 mL), and filter. Rotoevaporate the filtrate to give a black oil. Reflux the oil with collidine (19.7 mL, 18.1 g, 0.149 mole) and benzyl alcohol (15.4 mL, 16.1 g, 0.149 mole) in diglyme (150 mL) for 90 minutes under a N2 atmosphere. Cool to room temperature. Remove the diglyme by vacuum short path distillation. Add 10% aqueous citric acid (300 mL) and ethyl acetate (300 mL), filter, and separate the layers. Extract with ethyl acetate. Wash the organic solution with water, saturated NaCl, dry with MgSO4, filter and rotoevaporate to give a black liquid.

Dissolve the liquid in dichloromethane, and chromatograph on silica gel, eluting with ethyl acetate:hexane (1:4). Combine the appropriate fractions, and concentrate under reduced pressure to give the title compound (K) as an orange solid (15.63 g).

Step 2: (Phenylmethyl) 2-(3-(5-bromo-2-chloro)pyridyl)-2,2-dimethylacetate (Compound L)

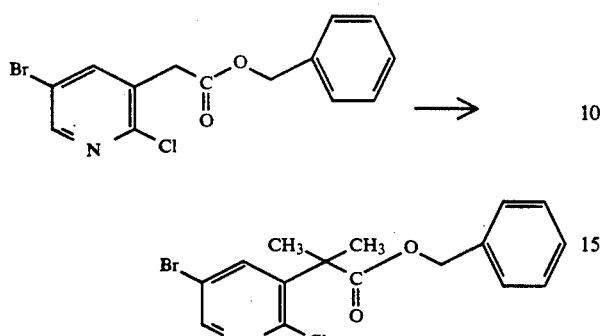

Add iodomethane (8.6 mL, 19.5 g, 0.138 mole) to sodium hydride (4.04 g of 60 weight-percent (wt %) NaH in oil, 0.101 mole, washed with hexane) in dry THF (100 mL) cooled to 0° C. under a N$_2$ atmosphere. Add benzyl 2-(3-(5-bromo-2-chloro)-pyridyl)acetate (15.6 g, 0.0459 mole) in dry THF (75 mL) dropwise by addition funnel at less than 10° C. Let the reaction mixture warm up slowly, and stir for 20 hours at room temperature. Add saturated NH$_4$Cl (50 mL), and rotoevaporate. Add water (150 mL), and extract with dichloromethane. Wash the organic solution with saturated NaCl, dry with MgSO$_4$, filter and rotoevaporate to give a brown liquid. Dissolve the liquid in dichloromethane, and chromatograph on silica gel, eluting with ethyl acetate:hexane (1:4). Combine the appropriate fractions, and concentrate under reduced pressure to give the title compound(L) as a orangish-brown liquid (13.7 g).

Step 3: 2-(3-(bromo-2-chloro)-pyridyl)-2,2-dimethylacetic acid (Compound M)

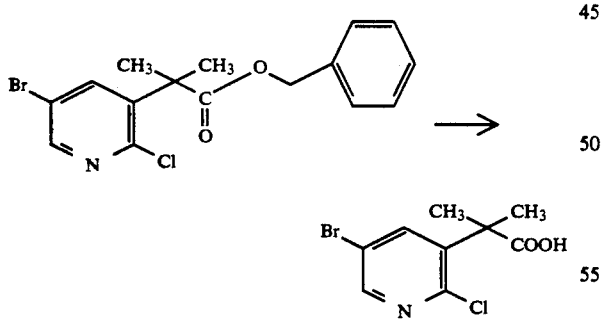

Reflux phenylmethyl 2-(3-(5-bromo-2-chloro)-pyridyl)-2,2-dimethylacetate (9.70 g, 0.0263 mole) and sodium hydroxide (3.16 g, 0.0789 mole) in THF (50 mL), water (50 mL), and methanol (25 mL) for 24 hours. Cool to room temperature, and rotoevaporate. Add water (100 mL), and wash with diethyl ether. Acidify to pH=3 with concentrated HCl, and extract with dichloromethane. Dry the organic solution with MgSO$_4$, filter, and rotoevaporate to give the title compound (M) as a yellow solid (6.62 g).

Step 4. 5-bromo-1,3-dihydro-3,3-dimethyl-N-(4-chlorophenyl)-2H-pyrrolo(2,3-b)-pyridin-2-one (Compound MM)

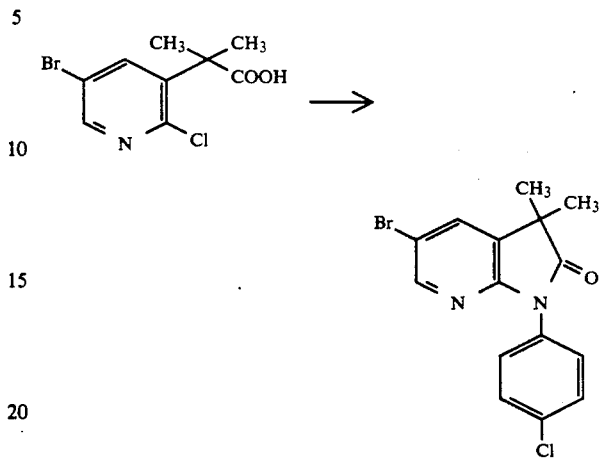

Add oxalyl chloride (4.7 ml, 6.90 g, 54.4 mmole) to 2-(3-(5-bromo-2-chloro)-pyridyl)-2,2-dimethylacetic acid (5.05 g, 18.13 mmole) in dry THF (70 mL) at 0° C. under a nitrogen atmosphere. Stir for 30 minutes at 0° C., and then stir for 18 hours at room temperature. Rotoevaporate the reaction mixture. Add THF (20 mL), and rotoevaporate again to give an oil. In a first flask, dissolve the oil in dry THF (30 mL), and cool to −78° C. under a nitrogen atmosphere. In a second flask, add n-butyl lithium (18.1 mL, 2.5M in THF, 45.33 mmole) to p-chloroaniline (6.01 g, 47.14 mmole) in dry THF (50 mL) at less than −50° C. under a nitrogen atmosphere, and stir for 30 minutes at −78° C. Add the p-chloroaniline anion solution to the first flask via cannula under nitrogen pressure. Warm the reaction mixture up slowly, and stir for 14 hours at room temperature. Add 1N HCl (50 mL), and rotoevaporate. Add water (50 mL) and extract with dichloromethane. Wash the organic solution with saturated NaCl, dry with MgSO$_4$, filter, and rotoevaporate to give a brown solid. Dissolve the solid in dichloromethane, and chromatograph on silica gel, eluting with ethyl acetate:hexane(1:4) then ethyl acetate:hexane (1:3). Combine the appropriate fractions, and concentrate under reduced pressure to give a solid. Recrystallize with isopropyl ether to give the title compound (MM), a white solid (3.39 g, m.p. 190° C.).

E: 2-[(4-Chlorophenyl)amino-a,a-dimethyl-3-pyridineacetic acid

Step 1: Methyl-2-[(4-chlorophenyl)amino-3-pyridinecarboxylate (Compound N)

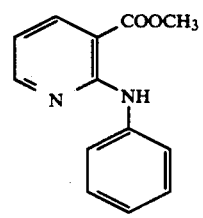

Reflux a mixture of 4-chloroaniline (24.6 g, 0.142 mole), methyl 2-chloro-3-pyridinecarboxylate (30.0 g, 0.175 mole), and triethylamine (19.4 g, 0.192 mole) in pentanol (250 mL) for 16 hours. Cool to room temperature, and remove pentanol by distillation. Add dichloromethane. Wash the organic solution with water, saturated aqueous NaHCO₃, and saturated aqueous NaCl, dry the organic solution with MgSO₄, filter, and rotoevaporate to give the title compound N.

Step 2: Methyl 2-[(4-chlorophenyl)(phenylmethyl)amino]-pyridinecarboxylate (Compound O)

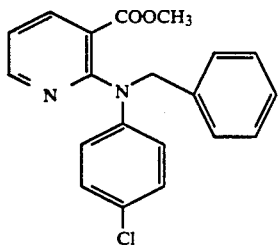

Add benzyl bromide (18.5 g, 12.9 mL, 0.108 mole) to sodium hydride (3.61 g of 60% NaH in oil, washed with hexane, 0.090 mole) in dry THF (200 mL) at 0° C. under a N₂ atmosphere. Add methyl-2-[(4-chlorophenyl)amino]-3-pyridinecarboxylate (N) (20.0 g, 0.072 mole) in dry THF (50 mL) dropwise by addition funnel. Warm the reaction mixture up slowly, and stir for 16 hours at reflux. Cool to room temperature, and rotoevaporate to remove the solvent. Add saturated aqueous NaHCO₃, and extract with ethyl acetate. Wash the organic solution with saturated aqueous NaCl, dry with MgSO₄, filter and rotoevaporate. Dissolve the oil in dichloromethane, and chromatograph on silica gel, eluting with ethyl acetate-hexane. Combine the appropriate fractions, and concentrate under reduced pressure to give the title compound O.

Step 3: 2-[(4-Chlorophenyl)(phenylmethyl)amino]-3-pyridinecarboxylic acid (Compound P)

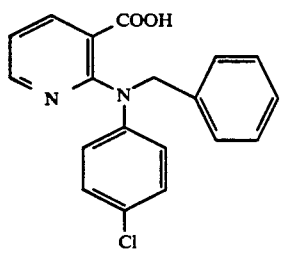

Reflux methyl 2-[(4-chlorophenyl)(phenylmethyl)amino]-3-pyridinecarboxylate (O) (20.0 g, 0.055 mole) and sodium hydroxide (6.54 g, 0.164 mole) in THF (70 mL), water (70 mL), and methanol (60 mL) for 16 hours. Cool to room temperature, and rotoevaporate. Add water, and wash with diethyl ether. Acidify to pH=3 with concentrated HCl, and extract with dichloromethane. Dry the organic solution with MgSO₄, filter and rotoevaporate to give the title compound P.

Step 4: (Phenylmethyl) 2-[(4-chlorophenyl)(phenylmethyl)amino]-3-pyridineacetate (Compound O)

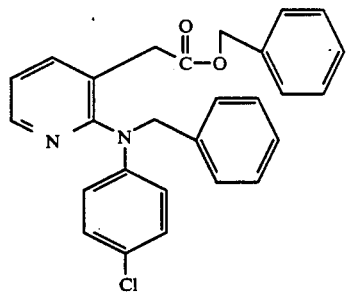

Add oxalyl chloride (16.2 g, 11.1 mL, 0.128 mole) to 2-[(4-chlorophenyl)(phenylmethyl)amino]-3-pyridinecarboxylic acid (P) (15.0 g, 0.043 mole) in dry THF (175 mL) at 0° C. under a N₂ atmosphere. Stir for 30 minutes at 0° C., and then stir 18 hours at room temperature. Rotoevaporate the reaction mixture. Add THF and rotoevaporate again. Dissolve the oil in THF (75 mL) and acetonitrile (75 mL), and cool to 0° C. under a N₂ atmosphere. Add triethylamine (8.60 g, 11.9 mL, 0.085 mole) and then trimethylsilydiazomethane (5.83 g, 46.9 mL of a 10% by weight solution in dichloromethane, 0.051 mole) dropwise by addition funnel at less than 10° C. Stir for 5 hours at 0° C., and then warm slowly to room temperature. Stir for 16 hours at room temperature. Rotoevaporate the reaction mixture, add diethyl ether, and filter. Rotoevaporate the filtrate. Reflux the oil with collidine (10.3 g, 11.2 mL, 0.085 mole) and benzyl alcohol (9.19 g, 8.8 mL, 0.085 mole) in diglyme (85 mL) for 90 minutes under a N₂ atmosphere. Cool to room temperature. Remove the diglyme by vacuum short path distillation. Add 10% aqueous citric acid and ethyl acetate, filter, and separate the layers. Extract with ethyl acetate. Wash the organic solution with water, saturated aqueous NaCl, dry with MgSO₄, filter, and rotoevaporate. Dissolve the oil in dichloromethane, and chromatograph on silica gel, eluting with ethyl acetate-hexane. Combine the appropriate fractions, and concentrate under reduced pressure to give the title compound Q.

Step 5: (Phenylmethyl) 2-[(4-chlorophenyl)(phenylmethyl)amino]-a,a-dimethyl-3-pyridineacetate (Compound R)

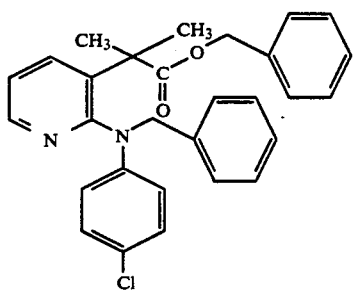

Add iodomethane (9.6 g, 4.2 mL, 0.068 mole) to sodium hydride (1.99 g of 60 wt % NaH in oil, washed with hexane, 0.050 mole) in dry THF (70 mL) cooled to 0° C. under a N₂ atmosphere. Add (phenylmethyl) 2-[(4- chlorophenyl)(phenylmethyl)amino]-3-pyridineacetate (Q) (10.0 g, 0.023 mole) in dry THF (30 mL) dropwise by addition funnel at less than 10° C. Warm the reaction mixture up slowly, and stir for 20 hours at room temperature. Add saturated NH4Cl, and rotoevaporate. Add water, and extract with dichloromethane. Wash the organic solution with saturated NaCl, dry with MgSO4, filter, and rotoevaporate. Dissolve the oil in dichloromethane, and chromatograph on silica gel, eluting with ethyl acetate-hexane. Combine the appropriate fractions, and concentrate under reduced pressure to give the title compound R.

Step 6:
2-[(4-Chlorophenyl)amino]-a,a-dimethyl-3-pyridineacetic acid (Compound S)

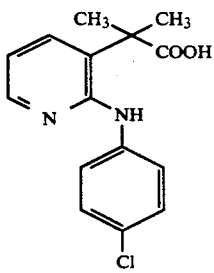

Add palladium on carbon catalyst (1.8 g) to (phenylmethyl) 2-[(4-chlorophenyl)(phenylmethyl)amino]-a,a,-dimethyl-3-pyridineacetate (R) (6.00 g, 0.013 mole) and ammonium formate (9.84 g, 0.156 mole) in methanol (100 mL). Stir at room temperature. Filter through celite to remove the catalyst, and wash with methanol. Rotoevaporate the filtrate. Add 1H NaOH, and wash with diethyl ether. Acidify to pH=3 with concentrated HCl, and extract with dichloromethane. Dry the organic solution with MgSO4, filter, and rotoevaporate to give the title compound S.

F:
1,3-Dihydro-3,3-dimethyl-2H-pyrrolo[2,3-b]pyridin-2-one (Compound T)

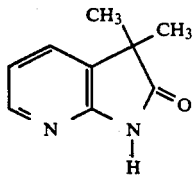

Add 1,3-dihydro-2H-pyrrolo[2,3-b]pyridin-2-one (8.50 g, 0.0634 mole) portionwise to sodium hydride (7.86 g of 60% NaH in oil, washed with hexane, 0.196 mole) in dry THF (300 mL) at 0° C. under a N2 atmosphere. Stir for 30 minutes at room temperature, and then cool to −78° C. Add iodomethane (7.9 mL, 17.99 g, 0.127 mole) dropwise, and warm reaction mixture up to room temperature slowly. Pour reaction mixture into saturated aqueous NH4Cl (250 mL), and rotoevaporate to remove THF. Extract the aqueous solution with ethyl acetate. Wash the organic solution with saturated aqueous NaCl, dry with MgSO4, filter, and rotoevaporate to give a yellow solid. Dissolve the solid in dichloromethane, and chromotograph on silica gel, eluting with ethyl acetate:hexane (1:1). Combine the appropriate fractions, and concentrate under a reduced pressure to give the title compound T as a white solid (5.17 g, m.p. 173°–174° C.).

EXAMPLE 1

1-(4-Chlorophenyl)-1,3-dihydro-3,3-dimethyl-2H-pyrrolo[2,3-b]pyridin-2-one (Compound U)

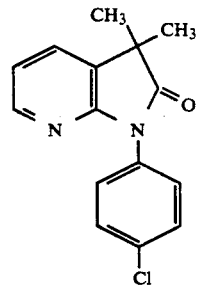

Add sodium hydride (7.8 g of 60% NaH in oil, washed with hexane, 0.195 mole) portionwise to 1-(4-chlorophenyl)-1,3-dihydro-2H-pyrrolo[2,3-b]pyridin-2-one (F) (23.2 g, 0.095 mole) in dry THF (850 mL) at 0° C. under a N2 atmosphere. Warm to room temperature, and stir for 15 minutes. Recool to 0° C. Add iodomethane (12.0 mL, 27.3 g, 0.193 mole) dropwise. Stir for 3 hours at 0° C. and for 1 hour at room temperature. Pour onto water (800 mL), and extract with dichloromethane. Dry the organic solution with MgSO4, filter, and rotoevaporate to give an oil. Triturate the oil with isopropyl ether several times. Dissolve the oil in dichloromethane, and chromatograph on silica gel, eluting with dichloromethane. Combine the appropriate fractions, and concentrate under reduced pressure to give a solid. Recrystallize with diethyl ether-isopropyl ether to give the title compound U as a white solid (9.85 g, m.p. 101°–102° C.).

Basically the same procedure as described above may be used to synthesize the compounds listed in Table 6 below:

TABLE 6

| R¹ | R² | R³ | m.p. (°C.) if solid |
|---|---|---|---|
| phenyl | CH3 | CH3 | 120–122 |
| (4-isopropyl)phenyl | CH3 | CH3 | 81–82 |
| isopropyl | CH3 | CH3 | oil (b.p. = 76–78° C. at 0 mmHg |
| 3-chlorophenyl | CH3 | CH3 | 120–122 |
| 4-fluorophenyl | CH3 | CH3 | 111–112 |
| 3-trifluoromethylphenyl | CH3 | CH3 | 102–103 |
| 4-bromophenyl | CH3 | CH3 | 135–137 |
| 2,4-dichlorophenyl | CH3 | CH3 | 94–95 |
| phenyl | C2H5 | C2H5 | 88–89 |
| 2-methyl-3-chlorophenyl | CH3 | CH3 | 129–130 |
| 4-methoxyphenyl | CH3 | CH3 | 108–109 |
| 2,4-difluorophenyl | CH3 | CH3 | 91–92 |
| 3,5-dichlorophenyl | CH3 | CH3 | 138–139 |

EXAMPLE 2

1,3-Dihydro-3,3-dimethyl-1-[4-(methylsulfinyl)phenyl]2H-pyrrolo[2,3-b]-pyridin-2-one (Compound V)

Add m-chloroperoxybenzoic acid (2.4 g of 80% 0.011 mole) portionwise to 1,3-dihydro-3,3-dimethyl-1-[4-(methylthio)phenyl]-2H-pyrrolo[2,3-b]pyridin-2-one (3.0 g, 0.011 mole) in dichloromethane (50 mL) at 5° C. to 10° C. Stir for 1 hour at 0° C. Pour onto ice (100 mL), and neutralize with saturated aqueous NaHCO$_3$. Extract the aqueous solution with dichloromethane, dry with MgSO$_4$, filter, and rotoevaporate to give a solid. Dissolve the solid in ethyl acetate, and chromatograph on silica gel, eluting with ethyl acetate and then methanol:dichloromethane (1:9). Combine the appropriate fractions, and concentrate under reduced pressure to an oil. Triturate with isopropyl ether to give the title compound V as a white solid (2.6 g, m.p. 133°–134° C.).

EXAMPLE 3

1,3-Dihydro-3,3-dimethyl-1-[4-methylsulfonyl)phenyl]2H-pyrrolo[2,3-b]-pyridin-2-one (Compound W)

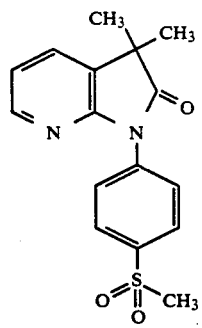

Add m-chloroperoxybenzoic acid (4.8 g of 80%, 0.022 mole) portionwise to 1,3-dihydro-3,3-dimethyl-1-[4-(methylthio)phenyl]-2H-pyrrolo[2,3-b]-pyridin-2-one (3.0 g, 0.011 mole) in dichloromethane (50 mL) at 0° C. Stir for 3 hours at 0° C. Pour onto ice water (50 mL), and neutralize with saturated aqeuous NaHCO$_3$. Extract the aqueous solution with MgSO$_4$, filter, and rotoevaporate to give a solid. Dissolve the solid in ethyl acetate, and chromatograph on silica gel, eluting with ethyl acetate. Combine the appropriate fractions, and concentrate under reduced pressure to give a solid. Recrystallize with dichloromethane-petroleum ether to give the title compound W as a white solid (2.9 g, m.p. 180°–181° C.).

EXAMPLE 4

1,3-Dihydro-3,3-dimethyl-1-phenyl-2H-pyrrolo[2,3-b]pyridine-2-thione (Compound X)

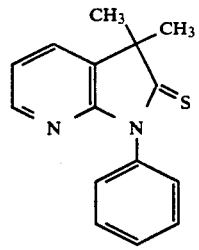

Reflux 1,3-dihydro-3,3-dimethyl-1-phenyl-2H-pyrrolo-[2,3-b]pyridin-2-one (2.0 g, 8.4 mmole) and Lawesson's reagent (2.06 g, 5.1 mmole) in dry toluene (11 mL) for 5 hours. Cool to room temperature, and rotoevaporate to remove solvent. Dissolve the residue in dichloromethane, and wash with water. Dry the organic solution with MgSO$_4$, filter, and rotoevaporate to give a soft solid. Dissolve the solid in dichloromethane, and chromatograph on silica gel, eluting with dichloromethane. Combine the appropriate fractions, and concentrate under reduced pressure to give a solid. Recrystallize with dichloromethane-petroleum ether to give the title compound (X) as a white solid (1.6 g, m.p. 152°–154° C.).

EXAMPLE 5

1,3-Dihydro-1,3,3-trimethyl-2H-pyrrolo[2,3-b]pyridin-2-one (Compound Y)

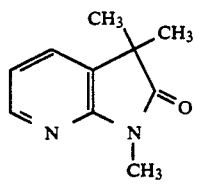

Add sodium hydride (20.5 g of 60% NaH in oil, 0.51 mole, washed with hexane) portionwise to 1,3-dihydro-2H-pyrrolo[2,3-b]-pyridin-2-one (19.3 g, 0.14 mole) in dry THF (800 mL) under a N$_2$ atmosphere. Stir for 5 minutes at room temperature, and then add iodomethane (30.8 mL, 70.3 g, 0.495 mole). Stir for 16 hours at room temperature. Pour the reaction mixture into ice water (500 mL), and extract with diethyl ether. Dry the organic solution with MgSO$_4$, filter, and rotoevaporate to give an oil. Triturate the oil with hot petroleum ether, filter, and rotoevaporate the filtrate to give a brown soft solid. Purify the crude product by vacuum short path distillation to give a solid (b.p. 73°–76° C. at 0.3 mmHg). Recrystallize with petroleum ether to give the title compound (Y) as a white solid (3.3 g, m.p. 59°–60° C.).

EXAMPLE 6

5-Bromo-1-(4-chlorophenyl)-1,3-dihydro-3,3-dimethyl-2H-pyrrolo[2,3-b]pyridine-2-one (Compound Z)

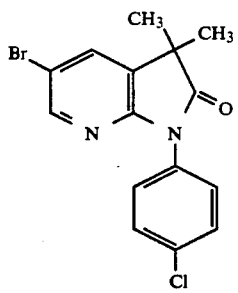

Add oxalyl chloride (4.74 mL, 6.90 g, 54.4 mmole) to 5-bromo-2-[(4-chlorophenyl)amino]-a,a-dimethyl-3,pyridineacetic acid (M) (5.05 g, 18.13 mmole) in dry THF (70 mL) at 0° C. under a $N_2$ atmosphere. Stir for 30 minutes at 0° C., and then stir for 18 hours at room temperature. Rotoevaporate the reaction mixture. Dissolve the solid in dichloromethane, and chromatograph on silica gel, eluting with ethyl acetate:hexane (1:4), then ethyl acetate:hexane (1:3). Combine the appropriate fractions, and concentrate under reduced pressure to give a solid. Recrystallize with isopropyl ether to give the title compound Z as a white solid (0.39 g, m.p. 190°–192° C.).

EXAMPLE 7

1,3-Dihydro-3-fluoro-3-methyl-1-phenyl-2H-pyrrolo[2,3-b]pyridin-2-one (Compound A)

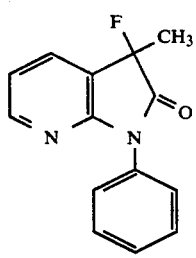

Add 1,3-dihydro-3-methyl-1-phenyl-2H-pyrrolo[2,3-b]-pyridin-2-one (H) (3.0 g, 0.013 mole) portionwise to sodium hydride (0.63 g of 60% NaH in oil, 0.015 mole, washed with hexane) in dry THF (35 mL) at 10° C. under a $N_2$ atmosphere. Stir for 30 minutes at room temperature, and then recool to 10° C. Add N-fluoro-N-neopentyl-p-toluenesulfonamide (4.1 g, 0.015 mole) in dry THF (30 mL) dropwise over 10 minutes. Warm reaction mixture up to room temperature slowly, and stir for 16 hours. Pour onto ice/water (100 mL), and neutralize to pH=4 to 5 with 15% aqueous HCl. Separate layers. Dry organic solution with MgSO4, filter, and rotoevaporate to give an oil. Dissolve the oil in dichloromethane, and chromatograph on silica gel, eluting with 30% ethyl acetate-hexane. Combine the appropriate fractions, and concentrate under reduced pressure. Triturate with isopropyl ether-petroleum ether and filter to give the title compound AA as a white solid (1.1 g, m.p. 83°–85° C.).

EXAMPLE 8

1-(4-Chlorophenyl)-1,3-dihydro-3,3-dimethyl-2H-pyrrolo[2,3-b]pyridin-2-one (Compound AB)

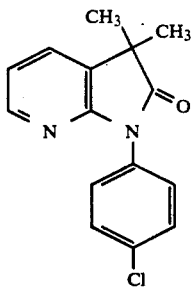

Add trifluoroacetic acid (5 mL) to 2-[(4-chlorophenyl)amino-a,a-dimethyl-3-pyridineacetic acid (S) (3.00 g, 0.010 mole) in dichloromethane (40 mL). Stir for 16 hours at room temperature. Rotoevaporate to remove the solvent. Add saturated organic solution with MgSO4, filter, and rotoevaporate. Dissolve the oil in dichloromethane, and chromatograph on silica gel, eluting with dichloromethane. Combine the appropriate fractions, and concentrate under reduced pressure to give a solid. Recrystallize with diethyl ether-isopropyl ether to give the title compound AB as a white solid.

EXAMPLE 9

1,3-Dihydro-3,3-dimethyl-1-(1-methylethyl-2H-pyrrolo-[2,3-b]pyridin-2-one (Compound AC)

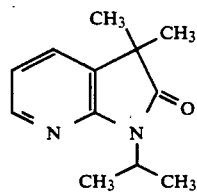

Add 1,3-dihydro-3,3-dimethyl-2H-pyrrolo[2,3-b]-pyridin-2-one (T) (5.00 g, 0.0308 mole) portionwise to sodium hydride (1.48 g of 60% NaH in oil, washed with hexane, 0.0370 mole) in dry THF (75 mL) at 0° C. under a $N_2$ atmosphere. Stir for 30 minutes at room temperature and then recool to 0° C. Add isopropyl bromide (5.68 g, 4.3 mL, 0.0462 mole) dropwise, and warm reaction mixture up to room temperature slowly. Stir for 16 hours at room temperature. Rotoevaporate to remove the solvent. Add saturated aqueous NaHCO3, and extract with ethyl acetate. Wash with saturated aqueous NaCl, dry the organic solution with MgSO4, filter, and rotoevaporate to give an oil. Dissolve the oil in dichloromethane, and chromatograph on silica gel, eluting with dichloromethane. Combine the appropriate fractions, and concentrate under reduced pressure to give an oil. Distill the oil to give the title compound AC.

EXAMPLE 10

1,3-Dihydro-3-[2-(acetoxy)-ethylthio]-3-(1-oxoethyl)-N-phenyl-2H-pyrrolo[2,3-b]pyridin-2-one Step 1:
3-[2-(hydroxy)-ethylthiomethyl]-N-phenyl-2-pyridinamine(Compound AD)

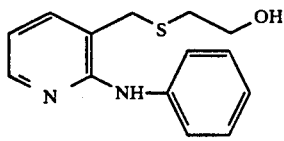

Add 2-mercaptoethanol (156.3 g, 2.00 mole) to a stirred solution of NaOH (172.5 g, 4.30 mole) in water (1.3 L) and ethanol (6.0 L). Stir for 30 minutes at room temperature and then cool to 15° C. Add portionwise 3-(chloromethyl)-N-phenyl-2-pyridinamine, hydrochloride (500.0 g, 1.96 mole) such that the internal temperature is below 20° C. Stir for 16 hours at room temperature. Concentrate the volume of the reaction mixture to approximately 2 L, and add water (1.5 L). Extract the aqueous solution with dichloromethane. Dry the organic extracts with MgSO4, filter and rotoevaporate to give the title compound as an oil (496.6 g).

Step 2:
3-[2-(t-butyldimethylsilyloxy)-ethylthiomethyl]-N-phenyl-2-pyridinamine(Compound AE)

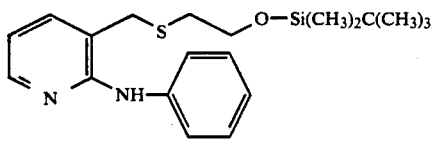

Reflux 3-[2-(hydroxy)-ethylthiomethyl]-N-phenyl-2-pyridinamine (12.40 g, 47.6 mmole), triethylamine (7.23 g, 10.0 mL, 71.4 mmole), t-butyldimethylsilyl chloride (7.90 g, 52.4 mmole), and 4-(N,N-dimethylamino)-pyridine (0.58 g, 4.76 mmole) in THF (200 mL) for 17 hours. Rotoevaporate to remove the solvent and add ethyl acetate (400 mL). Wash the organic solution with water, saturated aqueous NaHCO3, saturated aqueous NaCl, dry with MgSO4, filter, and rotoevaporate to give a yellow oil. Dissolve the oil in dichloromethane, and chromatograph on silica gel, eluting with ethyl acetate:hexane (1:8). Combine the appropriate fractions and concentrate under reduced pressure to give the title compound as a light yellow oil (15.69 g).

Step 3: Phenyl N-[2-(3-(2-(t-butyldimethylsilyloxy)ethylthiomethyl)-pyridyl]-N-phenyl-carbamate(Compound AF)

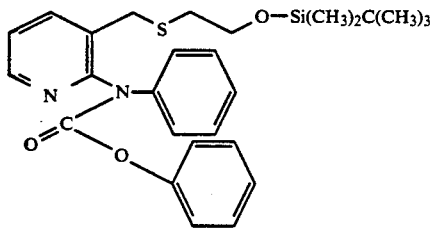

Add n-butyl lithium (8.3 mL, 20.6 mmole, 2.5M in hexane) to 3-[2-(t-butyldimethylsilyloxy)-ethylthiomethyl]-N-phenyl-2-pyridinamine (7.35 g, 19.6 mmole) in THF (75 mL) at −78° C. under nitrogen. Stir for 30 minutes at −78° C. Add phenyl chloroformate (3.69 g, 3.0 mL, 23.5 mmole), and let the reaction mixture warm slowly to room temperature. Rotoevaporate to remove the solvent, and add water (125 mL). Extract with ethyl acetate. Wash the organic extracts with aqueous saturated NaCl, dry with MgSO4, filter, and rotoevaporate to give a yellow liquid. Dissolve the liquid in dichloromethane, and chromatograph on silica gel, eluting with ethyl acetate:hexane (1:3). Combine the appropriate fractions, and concentrate to give the title compound as a colorless liquid (9.56 g).

Step 4. 2H-pyrrolo[2,3-b]pyridin-2-one(Compound AG)

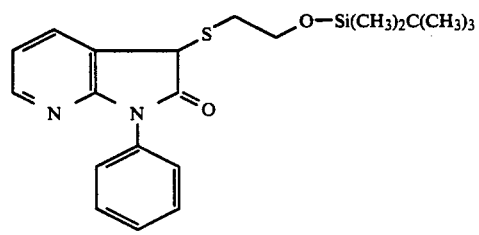

Add n-butyl lithium (15.7 mL, 39.3 mmole, 2.5 M in hexane) to diisopropylamine (4.26 g, 5.9 mL, 42.1 mmole) in THF (35 mL) at 0° C. under nitrogen. Stir for 15 minutes at 0° C., and cool to −78° C. Dissolve phenyl N-[2-(3-(2-(t-butyldimethylsilyloxy)-ethylthiomethyl)-pyridyl)]-N-phenyl-carbamate (9.26 g, 18.7 mmole) in THF (40 mL), and cool to −78° C. under nitrogen. Add lithium diisopropylamide solution to the carbamate solution via cannula under nitrogen pressure. Stir for two hours at −78° C. Add 25 wt % HCl in ethanol (7.5 mL), which is also cooled to −78° C., and water (50 mL). Rotoevaporate to remove the THF. Add water (50 mL) and 1N HCl (10 mL). Extract with ethyl acetate. Wash the organic extracts with aqueous saturated NaCl, dry with MgSO4, filter, and rotoevaporate to give a brown oil. Dissolve the oil in dichloromethane, and chromatograph on silica gel, eluting with ethyl acetate:hexane (1:3). Combine the appropriate fractions, and concentrate to give the title compound as a yellow oil (7.01 g).

Step 5:
1,3-Dihydro-3-[2-(hydroxy)-ethylthio]-N-phenyl-2H-pyrrolo[2,3-b]-pyridin-2-one(Compound AI)

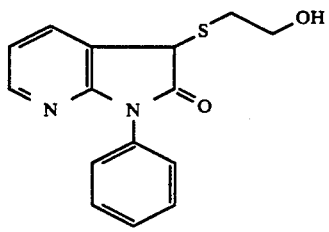

Add 20% aqueous HF (8 mL) to 1,3-dihydro-3-[2-(t-butyldimethyl-silyloxy)-ethylthio]-N-phenyl-2H-pyrrolo[2,3-b]pyridin-2-one (7.01 g, 17.5 mmole) in acetonitrile (70 mL) at 0° C. Warm to room temperature, and stir for two hours. Add aqueous saturated NaHCO3 (100 mL) carefully. Rotoevaporate to remove the acetonitrile. Extract with ethyl acetate. Wash the organic extracts with aqueous saturated NaCl, dry with MgSO4, filter, and rotoevaporate to give a green liquid. Dissolve the liquid in dichloromethane, and chromatograph on silica gel, eluting with ethyl acetate:hexane (1:2). Combine the appropriate fractions, and concentrate to give the title compound as a white solid (4.17 g, m.p. 107°–109° C.).

Step 6:
1,3-Dihydro-3-[2-(acetoxy)-ethylthio]-3-(1-oxoethyl)-N-phenyl-2H-pyrrolo[2,3-b]pyridin-2-one(Compound AJ)

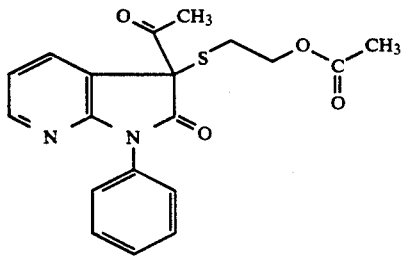

Add acetyl chloride (42.5 g, 38.5 mL, 0.542 mole) to 1,3-dihydro-3-[2-(hydroxy)-ethylthio]-N-phenyl-2H-pyrrolo[2,3-b]pyridin-2-one (70.5 g, 0.246 mole) and triethylamine (57.30 g, 78.9 mL, 0.566 mole) in dichloromethane (1.1 L) at 0° C. slowly such that the internal temperature is less then 20° C. Stir for two hours at 0° C. and for one hour at room temperature. Filter the reaction mixture, and wash the solid with dichloromethane. Wash the filtrate with aqueous saturated NaHCO3, treat with charcoal, dry with MgSO4, filter, and rotoevaporate to give a dark oil. Dissolve the oil in dichloromethane, and chromatograph on silica gel, eluting with ethyl acetate:hexane (1:1). Combine the appropriate fractions, and concentrate to give a reddish-brown oil. Crystallize the oil with isopropyl ether-petroleum ether, and recrystallize with diethyl ether-petroleum ether to give the title compound as a white solid (47.3 g, m.p. 69°–71° C.).

EXAMPLE 11

2-methoxy-N-phenyl-3-phenylthio-1H-pyrrolo(2,3-b)-pyridine

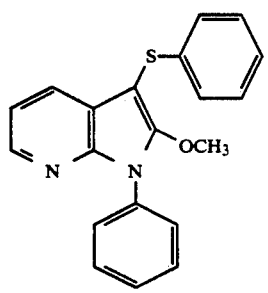

Add 1,3-dihydro-N-phenyl-3-(phenylthio)-2H-pyrrolo(2,3-b)pyridine (4.0 g, 12.6 mmole) portionwise to potassium hydride (KH) (1.73 g of 35 weight-percent KH in oil, washed with hexane, 15.1 mmole) in dry DMF (50 mL) at 0° C. under a nitrogen atmosphere. Stir for 45 minutes at 0° C. Add methyl tosylate(3.04 g, 16.3 mmole), and warm the reaction mixture up to room temperature slowly. Stir for 16 hours at room temperature. Remove DMF by high vacuum distillation. Add saturated aqueous NH4Cl (150 mL) and extract with ethyl acetate. Wash the organic extracts with saturated aqueous NaCl, dry with MgSO4, filter and rotoevaporate to give an oil. Dissolve oil in dichloromethane and chromatograph on silica gel, eluting with ethyl acetate:hexane (1:6). Combine appropriate fractions and concentrate under reduced pressure to give an oil. Crystallize the oil with diethyl ether-hexane to give the title compound as a white solid (1.05 g, m.p.=86°–87.5° C.).

While the present invention has been described in conjunction with the specific embodiments set forth above, many alternatives, modifications and variations therefore will be apparent to those of ordinary skill in the art. All such alternatives, modifications and variations are intended to fall within the spirit and scope of the present invention.

What is claimed is:

1. A compound of formula

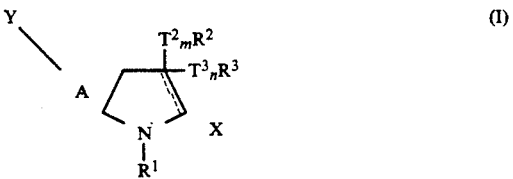

or a pharmaceutically acceptable salt or solvate thereof, wherein

A is selected from

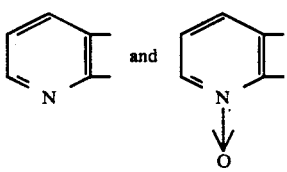

the dotted lines represent optional double bonds, such that
when the bond to X is a double bond, X is O or S; and
when the bond to X is a single bond, X is —OR$^{10}$ wherein R$^{10}$ is alkyl or aralkyl wherein one and only one of the pair of dotted lines must be a double bond;
T$^2$ and T$^3$ independently represent S, SO or SO$_2$;
m and n independently represent 0 or 1;
R$^1$ represents hydrogen, alkyl, aryl, aralkyl, or a 5- or 6-membered heterocyclic aromatic ring having from 1 to 3 heteroatoms in the ring, each heteroatom independently selected from NR$^6$, O, S or N atoms wherein R$^6$ is hydrogen or C$_1$ to C$_4$ alkyl;
R$^2$ and R$^3$ independently represent
hydrogen with the proviso at least one of R$^2$ and R$^3$ is not hydrogen; alkyl; cycloalkyl; halogen; haloalkyl; hydroxyalkyl; alkoxyalkyl; aryl; aralkyl; —COR$^7$ wherein R$^7$ is alkyl, aryl or aralkyl;
and with the further proviso that when T$^2_m$ or T$^3_n$ is S, SO or SO$_2$ that R$^2$ or R$^3$ is not hydrogen or halogen;
—D—OCO—R$^4$ wherein D represents an alkylene group having from 1 to 4 carbon atoms and R$^4$ is alkyl, aryl or aralkyl;

a C₃ to C₇ spirocarbocyclic ring whereby R² and R³ are joined together;

the rings represented by A, R¹, aryl or aralkyl may each be optionally substituted by up to three Y substituents;

wherein each Y substituent independently represents —OH, hydroxyalkyl, alkyl, halogen, —NO₂, alkoxy, alkoxyalkyl, —CF₃, —CN, cycloalkyl, alkynyloxy, alkenyloxy, —S(O)$_p$—R⁴ (wherein R⁴ is defined above and p is an integer from 0 to 2), —CO—R⁵ (wherein R⁵ represents —OH, —NH₂, —NHR⁴, N(R⁴)₂ or —OR⁴ in which R⁴ is as defined above), —O—D—COR⁵ (wherein D is defined above and R⁵ is as defined above), —NH₂, —NHR⁴, —N(R⁴)₂ (wherein R⁴ is as defined above) or —NHC(O)H with the proviso in formula I that if:
X is oxygen;
A is

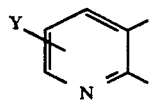

Y, if present is alkyl;
at least one of R² and R³ is alkyl or halogen; then
R¹ cannot be hydrogen.

2. A compound according to claim 1, wherein X is O.

3. A compound according to claim 2, wherein A represents

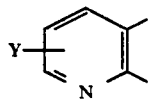

4. A compound according to claim 3, wherein R¹ represents alkyl, phenyl, substituted phenyl, 2-, 3- or 4-pyridyl, 2- or 3-furyl, 2- or 3-thienyl, 2-, 4- or 5-thiazolyl or 2- or 4-imidazolyl.

5. A compound according to claim 4, wherein substituted phenyl represents a phenyl ring substituted with 1 to 3 Y groups each independently selected from chloro, fluoro, alkyl, —CF₃, alkoxy, alkylsulfinyl, alkylthio, or alkylsulfonyl.

6. A compound according to claim 5, wherein R² and R³ are the same or different and each is selected from CH₃, C₂H₅ or F.

7. A compound according to claim 4, wherein R² and R³ both represent CH₃.

8. The compound of claim 1 of the formula

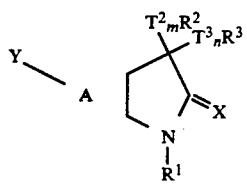
(Ivi)

wherein Y, A, T², T³, X, m, n, R¹, R² and R³ are as defined hereinbefore.

9. The compound of claim 8 wherein A is

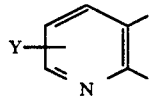

Y is H, T² is S, n is zero, X is O and R¹, R³ and m are as defined hereinbefore.

10. A compound of the formula

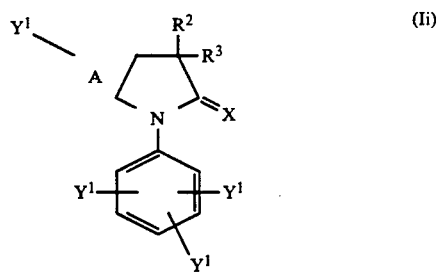
(Ii)

wherein
ring A represents

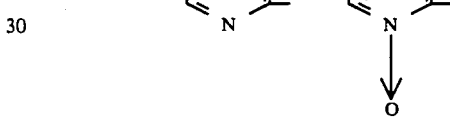

each Y¹ independently represents hydrogen, chloro, fluoro, methoxy, methylthio, methylsulfinyl and methylsulfonyl;

R² and R³ are independently selected from methyl, ethyl and fluoro; and

X is O or S.

11. A compound according to claim 7, wherein ring A is

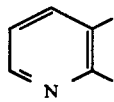

12. A compound according to claim 11, wherein X is O.

13. A compound which is
1-(4-chlorophenyl)-1,3-dihydro-3,3-dimethyl-2H-pyrrolo[2,3-b]pyridin-2-one,
1,3-dihydro-3,3-dimethyl-1-[4-(methylsulfinyl)phenyl]-2H-pyrrolo[2,3-b]pyridin-2-one,
1,3-dihydro-3,3-dimethyl-1-[4-(methylsulfonyl)phenyl]-2H-pyrrolo[2,3-b]pyridin-2-one,
1,3-dihydro-3,3-dimethyl-1-phenyl-2H-pyrrolo[2,3-b]-pyridine-2-thione,
1,3-dihydro-1,3,3-trimethyl-2H-pyrrolo[2,3-b]pyridin-2-one,
5-bromo-1,3-dihydro-3,3-dimethyl-1-(4-chlorophenyl)-2H-pyrrolo[2,3-b]pyridin-2-one,
1,3-dihydro-3-fluoro-3-methyl-1-phenyl-2H-pyrrolo[2,3-b]pyridin-2-one,
1,3-dihydro-3,3-dimethyl-1-(1-methylethyl)-2H-pyrrolo[2,3-b]pyridin-2-one, 1,3-dihydro-3,3-dimethyl-1-phenyl-2H-pyrrolo[2,3-b]pyridin-2-one,
1,3-dihydro-3,3-dimethyl-1[4-(1-methylethyl)-phenyl]-2H-pyrrolo[2,3-b]pyridin-2-one,
1-(3-chlorophenyl)-1,3-dihydro-3,3-dimethyl-2H-pyrrolo[2,3-b]pyridin-2-one,
1-(3,4-dichlorophenyl)-1,3-dihydro-3,3-dimethyl-2H-pyrrolo[2,3-b]pyridin-2-one,
1,3-dihydro-3,3-dimethyl-1-(4-fluorophenyl)-2H-pyrrolo[2,3-b]pyridin-2-one,
1,3-dihydro-3,3-dimethyl-1-[4-(methylthio)phenyl]-2H-pyrrolo[2,3-b]pyridin-2-one,
1,3-dihydro-3,3-dimethyl-1-[3-(trifluoromethyl)-phenyl]-2H-pyrrolo[2,3-b]pyridin-2-one,
1-(4-bromophenyl)-1,3-dihydro-3,3-dimethyl-2H-pyrrolo[2,3-b]pyridin-2-one,
1-(2,4-dichlorophenyl)-1,3-dihydro-3,3-dimethyl-2H-pyrrolo[2,3-b]pyridin-2-one,
1,3-dihydro-3,3-diethyl-1-phenyl-2H-pyrrolo[2,3-b]-pyridin-2-one,
1,3-dihydro-3,3-dimethyl-1-(2-methyl-3-chlorophenyl)-2H-pyrrolo[2,3-b]pyridin-2-one,
1,3-dihydro-3,3-dimethyl-1-(4-methoxyphenyl)-2H-pyrrolo[2,3-b]pyridin-2-one,
1-(2,4-difluorophenyl)-1,3-dihydro-3,3-dimethyl-2H-pyrrolo[2,3-b]pyridin-2-one,
1-(3,5-dichlorophenyl)-1,3-dihydro-3,3-dimethyl-2H-pyrrolo[2,3-b]pyridin-2-one,
1,3-dihydro-1-phenyl-3-(phenylthio)-2H-pyrrolo[2,3-b]pyridin-2-one,
1,3-dihydro-3-(phenylthio)-1-(3-trifluoromethyl-phenyl)-2H-pyrrolo[2,3-b]pyridin-2-one,
1,3-dihydro-3-(phenylsulfinyl)-1-(3-trifluoromethyl-phenyl)-2H-pyrrolo[2,3-b]pyridin-2-one,
1,3-dihydro-1-(methylethyl)-3-(phenylthio)-2H-pyrrolo[2,3-b]pyridin-2-one,
1,3-dihydro-1-(4-(1-methylethyl)-phenyl)-3-(phenylthio)-2H-pyrrolo[2,3-b]pyridin-2-one,
2-methoxy-1-phenyl-3-(phenylthio)-1H-pyrrolo[2,3-b]pyridine,
1,3-dihydro-3-methyl-1-phenyl-3-(phenylthio)-2H-pyrrolo[2,3-b]pyridin-2-one,
1,3-dihydro-1-methyl-3-(phenylthio)-2H-pyrrolo[2,3-b]pyridin-2-one,
1,3-dihydro-1-(3-chloro-2-methylphenyl)-3-(phenylthio)-2H-pyrrolo[2,3-b]pyridin-2-one,
1,3-dihydro-3-(4-chlorophenylthio)-1-phenyl-2H-pyrrolo[2,3-b]pyridin-2-one,
1,3-dihydro-3-(2-chlorophenylthio)-1-phenyl-2H-pyrrolo[2,3-b]pyridin-2-one,
1,3-dihydro-3-(4-methoxyphenylthio)-1-phenyl-2H-pyrrolo[2,3-b]pyridin-2-one,
1,3-dihydro-3-(2-methoxyphenylthio)-1-phenyl-2H-pyrrolo[2,3-b]pyridin-2-one,
1,3-dihydro-3-(2-methylphenylthio)-1-phenyl-2H-pyrrolo[2,3-b]pyridin-2-one,
1,3-dihydro-1-methyl-3-(phenylsulfinyl)-2H-pyrrolo[2,3-b]pyridin-2-one,
1,3-dihydro-3-(2-hydroxyethylthio)-1-phenyl-2H-pyrrolo[2,3-b]pyridin-2-one,
1,3-dihydro-3,3-(diphenylthio)-1-(phenylmethyl)-2H-pyrrolo[2,3-b]pyridin-2-one,
1,3-dihydro-1-(phenylmethyl)-3-(phenylthio)-2H-pyrrolo[2,3-b]pyridin-2-one,
1,3-dihydro-3-[2-(acetoxy)-ethylthio]-3-(1-oxoethyl)-1-phenyl-2H-pyrrolo[2,3-b]pyridin-2-one,
1,3-dihydro-3-[2-hydroxyethylthio]-3-(1-oxoethyl)-1-phenyl-2H-pyrrolo[2,3-b]pyridin-2-one,
1,3-dihydro-3-[2-(acetoxy)-ethylthio]-1-phenyl-2H-pyrrolo[2,3-b]pyridin-2-one,
1,3-dihydro-1-methyl-3-(phenylsulfonyl)-2H-pyrrolo[2,3-b]pyridin-2-one,
1,3-dihydro-3-methyl-3-(methylthio)-1-phenyl-2H-pyrrolo[2,3-b]pyridin-2-one,
1,3-dihydro-1-(3-chlorophenyl)-3-(phenylthio)-2H-pyrrolo[2,3-b]pyridin-2-one or
1,3-dihydro-1-(3,4-dichlorophenyl)-3-(phenylthio)2H-pyrrolo[2,3-b]pyridin-2-one.

14. 1-(4-chlorophenyl)-1,3-dihydro-3,3-dimethyl-2H-pyrrolo[2,3-b]pyridin-2-one.

15. 1,3-dihydro-3,3-dimethyl-1-(4-fluorophenyl)-2H-pyrrolo[2,3-b]pyridin-2-one.

16. 1,3-dihydro-3,3-dimethyl-1-(4-methoxyphenyl)-2H-pyrrolo[2,3-b]pyridin-2-one.

17. A pharmaceutical composition comprising a compound of formula I as defined in claim 1 in combination with a pharmaceutically acceptable carrier.

18. A method for treating inflammation in a mammal comprising administering to said mammal an anti-inflammatory effective amount of a compound of formula I as defined in claim 1.

19. A method for treating psoriasis in a mammal comprising administering to said mammal an amount effective amount of a compound of formula I as defined in claim 1 effective to control psoriasis.

20. A method for treating allergic condition in a mammal comprising administering to said mammal an anti-allergic effective amount of a compound of formula I as defined in claim 1.

* * * * *

UNITED STATES PATENT AND TRADEMARK OFFICE
CERTIFICATE OF CORRECTION

PATENT NO. : 5,182,289

DATED : January 26, 1993

INVENTOR(S) : Ting, et al.

It is certified that error appears in the above-identified patent and that said Letters Patent is hereby corrected as shown below:

In column 2, line 5, and in column 13, line 5, delete

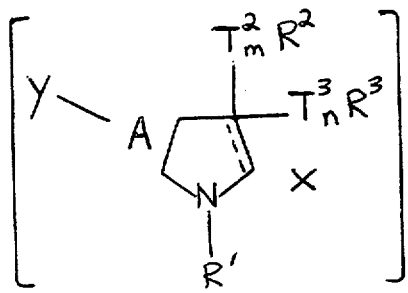 and insert in place therefor 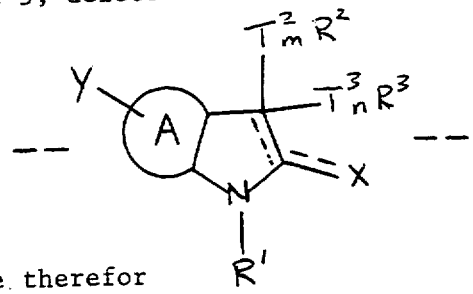

In column 2, line 15; in column 17, line 20; in column 5, line 50; and in column 17, line 5; delete

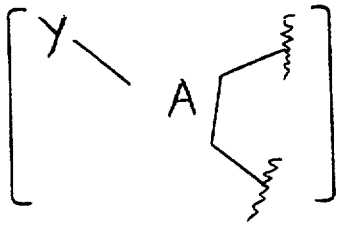 and insert in place therefor 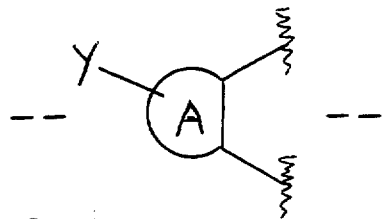

UNITED STATES PATENT AND TRADEMARK OFFICE
CERTIFICATE OF CORRECTION

PATENT NO. : 5,182,289

DATED : January 26, 1993

INVENTOR(S) : Ting, et al.

Page 2 of 4

It is certified that error appears in the above-identified patent and that said Letters Patent is hereby corrected as shown below:

In column 7, line 30; in column 13, line 15; in column 7, line 60; in column 13, line 35; in column 8, line 5; in column 13, line 50, in column 8, line 25; in column 13, line 65; in column 8, line 50; in column 14, line 10; in column 9, line 5; in column 14, line 30; in column 9, line 25; in column 14, line 45; in column 9, line 40; in column 10, line 30; in column 14, line 60; in column 15, line 40; in column 18, line 20; in column 9, line 50; in column 10, line 5; in column 12, line 5; in column 15, line 5; in column 15, line 15; in column 16, line 45; in column 18, line 10; in column 19, line 10 in column 10, line 15; in column 10, line 40; in column 15, line 30; in column 15, line 50; in column 10, line 60; in column 15, line 65; in column 11, line 5; in column 11, line 35; in column 16, line 10; in column 16, line 20; in column 11, line 45; in column 16, line 35; in column 12, line 15; in column 16, line 60; in column 12, line 40; in column 17, line 60; in column 17, line 65; in column 17, line 48; in column 17, line 52; and in column 18, line 5, delete

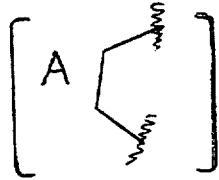 and insert in place therefor 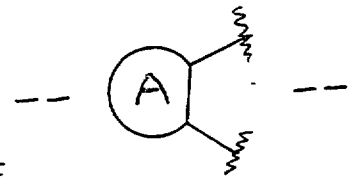

In column 12, line 50, delete

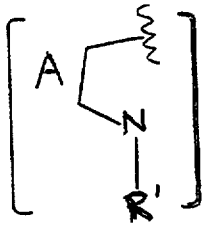 and insert in place therefor 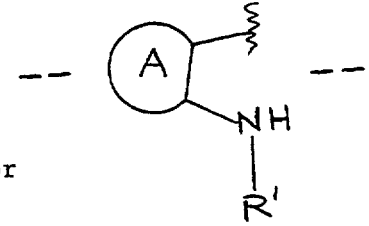

UNITED STATES PATENT AND TRADEMARK OFFICE
CERTIFICATE OF CORRECTION

PATENT NO. : 5,182,289

DATED : January 26, 1993

INVENTOR(S) : Ting, et al.

It is certified that error appears in the above-identified patent and that said Letters Patent is hereby corrected as shown below:

In column 45, line 64, delete "rolo(2,3-b)pyridine" and insert in place therefor --rolo[2,3-b]pyridin-2-one--.

In column 50, line 11, delete "3,3-(diphenylthio)" and insert in place therefor --3,3-di(phenylthio)--.

In column 50, lines 43-44 delete "amount effective".

In column 46, line 65, after "halogen;" insert --or--.

In column 47, line 1, before "a C3 to C7 spirocyclic ring" insert --or when m=n=o,--.

UNITED STATES PATENT AND TRADEMARK OFFICE
CERTIFICATE OF CORRECTION

PATENT NO. : 5,182,289
DATED : January 26, 1993
INVENTOR(S) : Ting, et al.

It is certified that error appears in the above-identified patent and that said Letters Patent is hereby corrected as shown below:

In column 5, line 5, delete

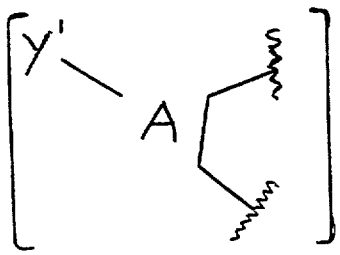 and insert in place therefor 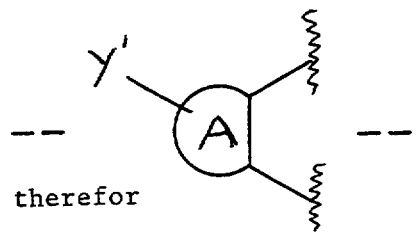

Signed and Sealed this

Eighth Day of November, 1994

Attest:

BRUCE LEHMAN

Attesting Officer

Commissioner of Patents and Trademarks